US009994886B2

(12) United States Patent
Dorsky

(10) Patent No.: US 9,994,886 B2
(45) Date of Patent: Jun. 12, 2018

(54) MODIFIED EPSTEIN-BARR VIRUS DNA POLYMERASE AND METHODS FOR ISOTHERMAL DNA AMPLIFICATION

(71) Applicant: University of Connecticut, Farmington, CT (US)

(72) Inventor: David Isaac Dorsky, Avon, CT (US)

(73) Assignee: THE UNIVERSITY OF CONNECTICUT, Farmington, CT (US)

( * ) Notice: Subject to any disclaimer, the term of this patent is extended or adjusted under 35 U.S.C. 154(b) by 388 days.

(21) Appl. No.: 14/466,426

(22) Filed: Aug. 22, 2014

(65) Prior Publication Data

US 2015/0064747 A1    Mar. 5, 2015

Related U.S. Application Data

(60) Provisional application No. 61/872,327, filed on Aug. 30, 2013.

(51) Int. Cl.
*C12P 19/34* (2006.01)
*C12N 9/12* (2006.01)
*C07K 14/005* (2006.01)

(52) U.S. Cl.
CPC ............ *C12P 19/34* (2013.01); *C07K 14/005* (2013.01); *C12N 9/1252* (2013.01); *C12N 2710/16222* (2013.01)

(58) Field of Classification Search
None
See application file for complete search history.

(56) References Cited

U.S. PATENT DOCUMENTS 6,124,120 A    9/2000    Lizardi

FOREIGN PATENT DOCUMENTS

WO    2012097318 A2    7/2012

OTHER PUBLICATIONS

Tsurumi et al., J. of Virology, vol. 68, No. 5, pp. 3354-3363, May 1994.*
Tsurumi, The Biochemical Journal, vol. 280, No. 5, pp. 703-708, 1991.*
Aliotta, J.M., et al., Thermostable Bst DNA polymerase I lacks a 3'-5' proofreading exonuclease activity. Genet Anal, 1996. 12(5-6): p. 185-95.
Alsmadi, O., et al., Specific and Complete Human Genome Amplification with Improved Yield Achieved by phi29 DNA Polymerase and a Novel Primer at Elevated Temperature. BMC Res Notes, 2009. 2: p. 48.
Aviel-Ronen, S., et al., Large fragment Bst DNA polymerase for whole genome amplification of DNA from formalin-fixed paraffin-embedded tissues. BMC Genomics, 2006. 7: p. 312.

Berman, A.J., et al., Structures of phi29 DNA polymerase complexed with substrate: the mechanism of translocation in B-family polymerases. EMBO J, 2007. 26(14): p. 3494-505.
Bernad, A., et al., A conserved 3'-5' exonuclease active site in prokaryotic and eukaryotic DNA polymerases. Cell, 1989 59(1): p. 219-28.
Bowman, G.D., et al., DNA polymerase clamp loaders and DNA recognition. FEBS Lett, 2005. 579(4): p. 863-7.
Burtt, N.P., Whole-genome amplification using Phi29 DNA polymerase. Cold Spring Harb Protoc, 2011. 2011(1): p. pdb prot5552.
Crute, J.J., E.S. Mocarski, and I.R. Lehman, A DNA helicase induced by herpes simplex virus type 1. Nucleic Acids Res, 1988. 16(14A): p. 6585-96.
De Vega, M., et al., Improvement of phi29 DNA polymerase amplification performance by fusion of DNA binding motifs. Proc Natl Acad Sci U S A, 2010. 107(38): p. 16506-11.
Dean, F.B., et al., Comprehensive human genome amplification using multiple displacement amplification. Proc Natl Acad Sci U S A, 2002. 99(8): p. 5261-6.
Dean, F.B., et al., Rapid amplification of plasmid and phage DNA using Phi 29 DNA polymerase and multiply-primed rolling circle amplification. Genome Res, 2001. 11(6): p. 1095-9.
Dorsky, D.I. and C. Plourde, Resistance to Antiviral Inhibitors Caused by the Mutation S889A in the Highly-Conserved 885-GDTDS Motif of the Herpes Simplex Virus Type 1 DNA Polymerase. Virology, 1993. 195(2): p. 831-5.
Falkenberg, M., I.R. Lehman, and P. Elias, Leading and lagging strand DNA synthesis in vitro by a reconstituted herpes simplex virus type 1 replisome. Proc Natl Acad Sci U S A, 2000. 97(8): p. 3896-900.
Fixman, E.D., G.S. Hayward, and S.D. Hayward, Trans-Acting Requirements for Replication of Epstein-Barr Virus ori-Lyt. J Virol, 1992. 66(8): p. 5030-9.
Hall, J.D., et al., Reduced in vivo mutagenesis by mutant herpes simplex DNA polymerase involves improved nucleotide selection. Proc Natl Acad Sci U S A, 1985. 82(11): p. 3889-93.
Hutchison, C.A., 3rd, et al., Cell-free cloning using phi29 DNA polymerase. Proc Natl Acad Sci U S A, 2005. 102 (48): p. 17332-6.
Joyce, C.M. and S.J. Benkovic, DNA Polymerase Fidelity: Kinetics, Structure, and Checkpoints. Biochemistry, 2004. 43(45): p. 14317-24.
Kamtekar, S., et al., Insights into Strand Displacement and Processivity from the Crystal Structure of the Protein Primed DNA Polymerase of Bacteriophage phi29. Mol Cell, 2004. 16(4): p. 609-18.
Kamtekar, S., et al., The phi29 DNA polymerase:protein-primer structure suggests a model for the initiation to elongation transition. EMBO J, 2006. 25(6): p. 1335-43.
Kiehl, A. and D.I. Dorsky, Cooperation of EBV DNA Polymerase and EA-D(BMRF1) in Vitro and Colocalization in Nuclei of Infected Cells. Virology, 1991. 184(1): p. 330-40.
Kiehl, A. and D.I. Dorsky, Bipartite DNA-Binding Region of the Epstein-Barr Virus BMRF1 Product Essential for DNA Polymerase Accessory Function. J Virol, 1995. 69(3): p. 1669-77.

(Continued)

*Primary Examiner* — Richard G Hutson
(74) *Attorney, Agent, or Firm* — Liang, Frank & King LLP; Stanley Liang

(57) ABSTRACT

Modified Epstein Barr Virus DNA polymerase for use in nucleic acid amplification, including isothermal nucleic acid amplification, in vitro are provided. Methods using and kits comprising Epstein Barr Virus DNA polymerase and its variants of this invention for nucleic acid amplification in vitro, including isothermal DNA amplification, are also provided.

1 Claim, No Drawings

(56) References Cited

OTHER PUBLICATIONS

Kurzynska-Kokorniak, A., et al., DNA-directed DNA Polymerase and Strand Displacement Activity of the Reverse Transcriptase Encoded by the R2 Retrotransposon. J Mol Biol, 2007. 374(2): p. 322-33.

Liu, S., et al., Crystal Structure of the Herpes Simplex Virus 1 DNA Polymerase. J Biol Chem, 2006. 281(26): p. 18193-200.

Lizardi, P.M., et al., Mutation detection and single-molecule counting using isothermal rolling-circle amplification. Nat Genet, 1998. 19(3): p. 225-32.

Lu, S., et al., Probing Meiotic Recombination and Aneuploidy of Single Sperm Cells by Whole-Genome Sequencing. Science, 2012. 338(6114): p. 1627-30.

Manosas, M., et al., Mechanism of strand displacement synthesis by DNA replicative polymerases. Nucleic Acids Res, 2012. 40(13): p. 6174-86.

Manosas, M., et al., Collaborative coupling between polymerase and helicase for leading-strand synthesis. Nucleic Acids Res, 2012. 40(13): p. 6187-98.

Marcy, A.I., et al., Engineered Herpes Simplex Virus DNA Polymerase Point Mutants: the Most Highly Conserved Region Shared among alpha-like DNA Polymerases is Involved in Substrate Recognition. J Virol, 1990. 64(12): p. 5883-90.

Mori, Y., et al., Detection of Loop-Mediated Isothermal Amplification Reaction by Turbidity Derived from Magnesium Pyrophosphate Formation. Biochem Biophys Res Commun, 2001. 289(1): p. 150-4.

Murayama, K., et al., Crystal Structure of Epstein-Barr Virus DNA Polymerase Processivity Factor BMRF1. J Biol Chem, 2009. 284(51): p. 35896-905.

Niemz, A., T.M. Ferguson, and D.S. Boyle, Point-of-care nucleic acid testing for infectious diseases. Trends Biotechnol, 2011. 29(5): p. 240-50.

Notomi,, T., et al., Loop-mediated isothermal amplification of DNA. Nucleic Acids Res, 2000. 28(12): p. E63.

Pavlov, A.R., et al., Cooperation between Catalytic and DNA Binding Domains Enhances Thermostability and Supports DNA Synthesis at Higher Temperatures by Thermostable DNA Polymerases. Biochemistry, 2012. 51(10): p. 2032-43.

Randell, J.C. and D.M. Coen, Linear Diffusion on DNA Despite High-Affinity Binding by a DNA Polymerase Processivity factor. Mol Cell, 2001. 8(4): p. 911-20.

Rodriguez, I., et al., A specific subdomain in phi29 DNA polymerase confers both processivity and strand-displacement capacity. Proc Natl Acad Sci U S A, 2005. 102(18): p. 6407-12.

Salinas, F. and S.J. Benkovic, Characterization of bacteriophage T4-coordinated leading- and lagging-strand synthesis on a minicircle substrate. Proc Natl Acad Sci U S A, 2000. 97(13): p. 7196-201.

Steitz, T.A., Visualizing polynucleotide polymerase machines at work. EMBO J, 2006. 25(15): p. 3458-68.

Steitz, T.A. and Y.W. Yin, Accuracy, Lesion Bypass, Strand Displacement and Translocation by DNA Polymerases. Philos Trans R Soc Lond B Biol Sci, 2004. 359(1441): p. 17-23.

Akahashi H., et al., Cell-free cloning using multiply-primed rolling circle amplification with modified RNA primers. Biotechniques, 2009. 47(1): p. 609-15.

Tanner, N.A., Y. Zhang, and T.C. Evans, Jr., Simultaneous multiple target detection in real-time loop-mediated isothermal amplification. Biotechniques, 2012. 53(2): p. 81-9.

Tomita, N., et al., Loop-mediated isothermal amplification (LAMP) of gene sequences and simple visual detection of products. Nat Protoc, 2008. 3(5): p. 877-82.

Tsurumi, T., Characterization of 3'-to 5'-Exonuclease Activity Associated with Epstein-Barr Virus DNA Polymerase. Virology, 1991. 182(1): p. 376-81.

Tsurumi, T., Selective Inhibition of the 3'-to-5' Exonuclease Activity Associated with Epstein-Barr Virus DNA Polymerase by Ribonucleoside 5'-Monophosphates. Virology, 1992. 189(2): p. 803-7.

Tsurumi, T., et al., Functional interaction between Epstein-Barr Virus DNA Polymerase Catalytic Subunit and its Accessory Subunit in Vitro. J Virol, 1993. 67(12): p. 7648-53.

Tsurumi, T., T. Daikoku, and Y. Nishiyama, Further Characterization of the Interaction between the Epstein-Barr Virus DNA Polymerase Catalytic Subunit and its Accessory Subunit with Regard to the 3'-to-5' Exonucleolytic Activity and Stability of Initiation Complex at Primer Terminus. J Virol, 1994. 68(5): p. 3354-63.

Tsurumi, T., et al., Functional expression and characterization of the Epstein-Barr virus DNA polymerase catalytic subunit J Virol, 1993. 67(8): p. 4651-8.

Tsurumi, T., et al., Strand Displacement Associated DNA Synthesis Catalyzed by the Epstein-Barr Virus DNA Polymerase. Biochem Biophys Res Commun, 1997. 238(1): p. 33-8.

Viguera, E., D. Canceill, and S.D. Ehrlich, Replication slippage involves DNA polymerase pausing and dissociation. EMBO J, 2001. 20(10): p. 2587-95.

Wang, Y. et al. A novel strategy to engineer DNA polymerases for enhanced processivity and improved performance in vitro. Nucleic Acids Res, 2004. 32(3): p. 1197-207.

Yang, P.W., et al., Effect of phosphorylation on the transactivation activity of Epstein-Barr virus BMRF1, a major target of the viral BGLF4 kinase. J Gen Virol, 2008. 89(Pt 4): p. 884-95.

Zhang, Q., et al., Identification of transactivator and nuclear localization domains in the Epstein-Barr virus DNA polymerase accessory protein, BMRF1. J Gen Virol, 1999. 80 ( Pt 1): p. 69-74.

Zhang, Q., et al., The Epstein-Barr Virus (EBV) DNA Polymerase Accessory Protein, BMRF1, Activates the Essential Downstream Component of the EBV oriLyt. Virology, 1997. 230(1): p. 22-34.

Zhang, Q., et al., Functional and Physical Interactions between the Epstein-Barr Virus (EBV) Proteins BZLF1 and BMRF1: Effects on EBV Transcription and Lytic Replication. J Virol, 1996. 70(8): p. 5131-42.

Zhu, Y., et al., Kinetic Approaches to Understanding the Mechanisms of Fidelity of the Herpes Simplex Virus Type 1 DNA Polymerase. J Nucleic Acids, 2010. 2010: p. 631595.

Zhu, Y., et al., 3' to 5' Exonuclease Activity of Herpes Simplex Virus Type 1 DNA Polymerase Modulates its Strand Displacement Activity. J Virol, 2003. 77(18): p. 10147-53.

Zong, C., et al., Genome-Wide Detection of Single-Nucleotide and Copy-Number Variations of a Single Human Cell. Science, 2012. 338(6114): p. 1622-6.

Zuccola, H.J., et al., The Crystal Structure of an Unusual Processivity Factor, Herpes Simplex Virus UL42, Bound to the C Terminus of its Cognate Polymerase. Mol Cell, 2000. 5(2): p. 267-78.

International Search Report and Written Opinion from counterpart International Application No. PCT/US2014/052377, dated Nov. 28, 2014, 12 pages.

* cited by examiner

MODIFIED EPSTEIN-BARR VIRUS DNA POLYMERASE AND METHODS FOR ISOTHERMAL DNA AMPLIFICATION

CROSS REFERENCE TO RELATED APPLICATIONS

This application claims the benefit of priority from U.S. Provisional Application No. 61/872,327, filed on Aug. 30, 2013, the disclosure of which is incorporated by reference herein.

This invention was made with government support under NIH R29 AI29009 awarded by the National Institute of Health. The government has certain rights in the invention.

INCORPORATION OF SEQUENCE LISTING

The instant application contains a Sequence Listing, which has been submitted electronically in ASCII format and is hereby incorporated by reference in its entirety. Said ASCII copy, created on Aug. 21, 2014, is named 0900-USU1_SL.txt and is 21,406 bytes in size.

TECHNICAL FIELD OF THE INVENTION

This invention relates to the field of nucleic acid amplification.

BACKGROUND

Current DNA sequencing technology has made it both inexpensive and rapid to sequence whole genomes for a variety of important applications. The amount of available sample DNA, however, is often highly limited, thus requiring amplifying the DNA before sequencing. Genome amplification techniques generally utilize DNA polymerases that are capable of isothermally displacing DNA strands in concert with the DNA polymerization process.

The two most widely used strand displacing enzymes for DNA amplification are bacteriophage Phi29 (also denoted as Φ29) DNA polymerase ("DNApol") and BstI (also referred as Bst) DNA polymerase. These two enzymes are currently the gold standard for isothermal nucleic acid amplification.

The Φ29 DNA polymerase was used to develop multiply-primed rolling circle amplification using random hexamer primers. The Φ29 DNApol, a family B member, has high processivity, high fidelity, comparable to the best enzymes commercially available for PCR, due to its "proofreading" 3'-5' exonuclease activity, and significant strand displacement activity. Although not thermostable for PCR, the Φ29 DNA polymerase has a broad operational temperature range, extending down into typical room temperatures, allowing reactions to be carried out at ambient temperature. Recently, through protein domain "swapping and tagging," the Φ29 DNA polymerase has been engineered for increased processivity. The Φ29 DNApol activity, however, is not very tolerant of high ionic strength.

The family A member BstI DNA polymerase large fragment lacks intrinsic 3'-5' exonuclease activity; thus, its fidelity is significantly less than that of the Φ29 DNApol. The large fragment of the Bst DNApol is prepared by partial proteolysis of the native enzyme with subtilisin, which cleaves the 5' exonuclease moiety. BstI DNApol is thermostable, so that DNA amplification reactions can be carried out at 65° C., which may be useful for amplifying GC-rich targets, and it is possible to carry out sequential extension and melting reactions desirable for some applications. However, BstI DNA polymerase activity at 37° C. is 10-15% of its activity at 65° C. and it is inactivated by heating at 80° C. for 20 minutes. BstI DNApol large fragment activity is intolerant of ionic strength above 60 mM KCl; however, recently, engineered forms of BstI DNA polymerase have become available that will tolerate ionic strength up to 150 mM KCl.

Examples of published patent applications and issued patents related to DNA polymerases and their use in amplification of nucleic acid sequences include EP Publication No. EP 07112927; EP Publication No. EP 2210941; U.S. Pat. No. 5,576,204; and U.S. Pat. No. 6,124,120, the disclosures of each of which is incorporated by reference herein.

The current gold standard method for whole-genome amplification ("WGA") employs the error-prone BstI DNA polymerase, with an error rate of $10^{-4}$. This method, Multiple Looping-Based Amplification Cycles ("MALBAC"), only allows amplification of, at best 93% and less in many cases, of the human genome efficiently, for single-cell genome sequencing. The high error rate and the inability to amplify 100% of the genome are major technical challenges and significant disadvantages of this method.

Most DNA copying enzymes have a mis-incorporation (error) rate of $10^{-4}$, unless they have an intrinsic proofreading 3'-5' exonuclease, which BstI DNApol large fragment lacks. DNA polymerases with 3'-5' exonuclease domains typically are characterized by error rates of about $10^{-8}$. On the other hand, error rates typically increase to about $10^{-6}$ for DNA polymerases with site-specific exo-mutants. Exo-mutants often have increased elongation rates and increased processivity due to diminished "idling," and often have increased strand-displacement activities. An amplification error rate in the order of $10^{-8}$ dictates that tens of erroneous single-nucleotide changes could be introduced into an amplified single-cell genome. If single-cell genome amplification is being carried out for the purpose of detecting single nucleotide mutations, then multiple amplifications must be carried out and sequenced to show statistically that the changes are not due to the amplification method. It follows that the more error-prone the enzyme, the more error-prone the amplification method, and the greater the amount of duplication that will be necessary.

Some of the problems of amplification bias and introduction of copying errors are linked to intrinsic properties of the DNApol enzymes used to amplify the DNA to be sequenced. At present there is no single enzyme being used in these protocols with all of the properties of an ideal copier; thus there is a need for a different DNA polymerase possessing some critical characteristics. Of the many DNA polymerases that have been characterized, comparatively few possess significant strand-displacement activity ("SDA"), one characteristic necessary for WGA applications. The linkage of SDA to processivity and proofreading 3'-5' exonuclease activity appears also to be important.

Another desirable property for a DNA polymerase for use in amplifying nucleic acids in vitro (such as single-cell genome amplification) is tolerance (i.e., ability to function) of a broad range of salt concentrations ("salt tolerance"). Salt tolerance of an enzyme may allow considerable latitude and flexibility for designing new priming strategies, since priming involves hybridization, and hybridization conditions are highly salt sensitive.

SUMMARY OF THE INVENTION

This invention solves the problem discussed above by providing modified Epstein Barr Virus ("EBV") DNA polymerases (also referred to herein as EBV DNA polymerase variants) for use in nucleic acid amplification, including isothermal nucleic acid amplification, as well as methods and kits for using EBV DNA polymerase and EBV DNA polymerase variants to amplify nucleic acids in vitro.

In certain aspects, this invention provides a modified EBV DNA polymerase for use in nucleic acid amplification, which polymerase comprising nucleic acid amplification activity in vitro.

In other aspects, this invention provides a method for amplifying a target nucleic acid sequence in vitro. This method comprises mixing a set of primers with a target nucleic acid sample sequence and incubating the primer-target sample mixture under conditions that promote and/or optimize amplification of the target nucleic acid sequence during the next step; mixing an EBV DNA polymerase, including a modified EBV DNA polymerase of this invention, to produce a polymerase-primer-target sample mixture and incubating the polymerase-primer-target sample mixture under conditions that promote and/or optimize replication of the target sequence, wherein replication of the target sequence results in replicated strands, wherein during replication at least one of the replicated strands is displaced from the target sequence by strand displacement replication of another replicated strand.

In yet other aspects, this invention provides kits comprising an EBV DNA polymerase, including the modified EBV DNA polymerase of this invention, for use in nucleic acid amplification in vitro.

Numerous other aspects are provided in accordance with these and other aspects of the invention. Other features and aspects of the present invention will become more fully apparent from the following detailed description and the appended claims.

DETAILED DESCRIPTION OF THE INVENTION

In certain aspects, this invention provides modified EBV DNA polymerase ("EBVpol") enzymes for use in nucleic acid amplification, comprising nucleic acid amplification activity in vitro. In certain embodiments, the nucleic acid amplification is isothermal nucleic acid amplification. The nucleic acid can be any nucleic acid. In certain embodiments, the nucleic acid is DNA. In certain other embodiments, the nucleic acid is RNA. The nucleic acid amplification activity includes methods such as strand displacement DNA amplification, which includes strand displacement isothermal DNA amplification. EBVpol and its variants of this invention have strand displacement activities. The modified EBVpol can be modified by insertion of amino acid(s), deletion of amino acid(s), and/or substitution of amino acid(s) of the BMRF1 subunit and/or the BALF5 subunit. The substitution of amino acid(s) of the BMRF1 subunit and/or the BALF5 subunit can be from any amino acid residue to any other amino acid residue.

EBV DNA polymerase, a family B DNA polymerase, is a heterodimer with a 116-kilodaltons ("kDa") BALF5 catalytic subunit, with intrinsic 3'-5' exonuclease activity, and a 50-kDa BMRF1 subunit, which is a processivity factor. BMRF1 strongly binds to double stranded ("ds") DNA and binds in a very specific fashion to the BALF5 catalytic subunit, tethering the DNA polymerase holoenzyme complex to the primer-template junction. The BALF5 catalytic subunit possesses enzymatic activity capable of distributive (i.e., non-processive) extension of a primer-template substrate activity at low ionic strength, and a 3'-5' exonuclease proofreading function. When combined with the BMRF1 processivity factor, the EBV DNA polymerase holoenzyme exhibits highly processive primer-dependent DNA synthesis, with an ionic strength optimum at 150 mM ammonium sulfate and virtually no such activity at ionic strength below 10 mM ammonium sulfate. EBVpol has strong strand-displacing activity, and does so in the absence of any other protein factors. The BMRF1 processivity factor lacks any intrinsic enzymatic activity. The EBV DNA polymerase holoenzyme comprises a 1:1 complex of BALF5 and BMRF1; although BMRF1 dimerizes, it interacts with the BALF5 catalytic subunit as a monomer. Both subunits have been cloned and expressed as recombinant polypeptides, and can be obtained in highly-purified form. The DNA polymerase and the strand displacement functions of the resulting recombinant EBVpol enzyme are intact. It should be noted that a BMRF1 comprising a C95E mutation results in a monomeric form of BMRF1; this mutant protein can still efficiently catalyze EBVpol processivity.

Both the DNA and the amino acid sequences of BMRF1 and BALF5 are publicly available. The DNA sequence of the BMRF1 open reading frame ("ORF") is listed in the Sequence Listing as SEQ ID NO. 1 and the DNA sequence of the BALF5 ORF is SEQ ID NO. 2. The DNA sequence of a GST-BMRF1 (1-303), with a deletion of the DNA encoding the carboxyl-terminal 101 amino acids of BMRF1, is SEQ ID NO. 3. The skilled artisan can routinely arrive at the amino acid sequence of these three proteins based on the three DNA sequences provided. The amino acid sequence of the full-length BALF5 protein is provided as SEQ ID NO. 8 and the amino acid sequence of the full-length BMRF1 protein is provided as SEQ ID NO. 9.

In certain embodiments, the modified EBV DNA polymerase comprises one or more properties including high processivity, low error rate, salt tolerance (the ability to amplify DNA in a broad range of salt concentrations), the ability to amplify greater than about 95% of a DNA sequence, the ability to amplify greater than about 98% of a DNA sequence, and the ability to amplify greater than about any percentage in between 93%-98%.

Most DNA polymerases involved in genome replication, as opposed to DNA repair, function processively as a component of a multi-subunit replication complex operating at a replication fork in vivo. When a DNA polymerase molecule recognizes a DNA primer-template junction and initiates extension of the primer while copying the template, the length of DNA copied before the DNA polymerase dissociates from the DNA is a measure of the processivity of the enzyme. DNA polymerases that dissociate from the primer-template junction, and then re-initiate DNA synthesis are termed "distributive" enzymes, while enzymes that synthesize long tracts of DNA with a single initiation are termed "processive."

In certain embodiments, the modified EBV DNA polymerase comprises an insertion in the BALF5 subunit polypeptide. In certain embodiments, the modified EBV DNA polymerase comprises an insertion in the BMRF1 subunit polypeptide.

In certain embodiments, the modified EBV DNA polymerase comprises a deletion in the BALF5 subunit polypeptide. In some embodiments, the deletion in the BALF5 subunit is a carboxyl-terminal deletion, which can be a deletion of between about 10 to about 120 amino acids, or about 30 to about 70 amino acids, and any number of amino acids in between these ranges, including about 40, about 60, and about 112 amino acids.

In certain embodiments, the modified EBV DNA polymerase comprises a deletion in the BMRF1 subunit. In certain embodiments, the deletion mutant of BMRF1 is produced in a prokaryotic host cell, such as *E. coli*, and can be comprise an affinity tag, such as GST. In some embodiments, the deletion in the BMRF1 subunit is of residues 278-306. In certain embodiments, the deletion in the BMRF1 subunit is a carboxyl-terminal deletion. In some further embodiments, the carboxyl-terminal deletion of the BMRF1 subunit polypeptide is a deletion of residues 304-404. In yet other further embodiments, the carboxyl-terminal deletion of the BMRF1 subunit polypeptide is a deletion of between about 90 acids to about 110 amino acids, and any number of amino acids in between, including a deletion of about 100 to about 105 residues. The carboxyl-terminal 101 residues or so of BMRF1 are dispensible for in vitro DNA polymerase activity; this domain contains the BMRF1 nuclear localization signal and several serine and threonine phosphorylation sites that are substrates for cellular kinases and the EBV viral BGLF4 kinase.

In certain embodiments, the BMRF1 subunit polypeptide comprises one of the following deletions: a deletion of residues 124-217, residues 194-217, residues 206-236, residues 205-217, residues 206-236, residues 218-233, residues 238-276, or residues 278-306.

In certain embodiments, the modified EBV DNA polymerase comprises a BALF5 subunit comprising a mutation (substitution) at residue number 765 from Serine to Alanine (S765A).

In certain embodiments, the modified EBV DNA polymerase comprises a BALF5 subunit comprising a mutation (substitution) at residue 296 from Aspartic acid to Alanine (D296A); and/or at residue 298 from Glutamic acid to Alanine (E298A). In certain further embodiments, a double mutant BALF5 comprising both mutations (D296A and E298A) is also provided.

In certain other aspects, this invention provides a recombinant DNA molecule encoding a modified EBV DNA polymerase of this invention. This invention also provides a vector comprising this recombinant DNA molecule, such as a plasmid vector. In some embodiments, the plasmid vector comprising a recombinant DNA molecule encoding a modified EBV DNA polymerase of this invention allows expression of the modified EBV DNA polymerase in a suitable host cell. This invention also provides a host cell comprising this vector. The host cells include, for example, microbial host cells, such as bacterial cells (for example, *E. coli* and *Bacillus subtilis*), yeast cells (such as *Saccharomyces cerevisiae*), insect cells (such as Sf9 cells), mammalian cells (such as COS, CHO, HeLa, HEK, VERO, etc., cell lines), plant cells, and any other host cells that can be used to harbor recombinant DNA molecules. The recombinant host cells (cells that harbor a vector of this invention) are grown in the laboratory or in production by standard techniques, such as recombinant DNA techniques. The recombinant DNA molecules, the vectors, and the recombinant host cells are made using standard techniques, such as recombinant DNA techniques.

The EBVpol and the modified EBVpol of this invention can be part of a fusion protein, such as a fusion protein comprising an affinity tag, including, for example, a 6 histidine tag ("6× his," HHHHHH) (SEQ ID NO. 7), an HA tag, a GST tag, an maltose-binding protein domain ("MBP") tag, a MYC tag, etc. The affinity tag can be on the amino or the carboxyl terminus of EBVpol. The EBVpol and the modified EBVpol of this invention can be fused with any suitable protein, polypeptide, or peptide; the EBVpol and the modified EBVpol of this invention can be fused with any suitable other chemical compound, such as, for example, polyethyleneglycol, or sugar chains. In certain embodiments, the fusion protein comprises either BMRF1 or BALF5, including one of the modified EBVpol BMRF1 or BALF5 subunit of this invention, fused to DNA-interacting, membrane channel or tethering domains. In certain embodiments, the fusion protein comprises a carboxyl terminal deletion of either BMRF1 or BALF5, including those of this invention, fused at the N-terminus or at the C-terminus to a DNA-interacting, a membrane channel or a tethering protein or domain.

EBVpol and the modified EBVpol of this invention maintain their function at high salt concentrations, for example, up to about 160 mM ammonium sulfate. Such conditions of high ionic strength allow easier DNA strand displacement relative to isotonic conditions. EBVpol and the modified EBVpol of this invention maintain their function at high concentrations of a variety of salts, including, for example, KCl, NaCl, ammonium sulfate, other monovalent salts, or a mixture of such salts. The EBV polymerase is more salt tolerant than other strand-displacing DNA polymerases. This salt-tolerance advantageously enables methods to manipulate and optimize enzyme function by varying amplification or assay conditions. The salt-tolerance of the DNA polymerase can be manipulated, changed and adapted as needed for particular applications.

EBVpol and the modified EBVpol of this invention have strong amplification activity on GC-rich regions of DNA sequences; EBV DNA polymerase has 29-fold greater activity on synthetic oligo dG:poly dC (primer:template) compared to oligo dA:poly dT. GC-rich DNA sequences are the most difficult-to-amplify DNA sequences. Currently used DNA polymerases for isothermal amplification do not perform so well on GC-rich DNA. Thus, the GC-preference of EBVpol and its variants makes EBVpol and its variants preferred reagents for whole genome amplification ("WGA").

The modified EBVpol of this invention are useful in nucleic acid amplification. The modified EBVpol of this invention have a number of improved properties compared with enzymes currently used in nucleic acid amplification. The modified EBVpol enzymes of this invention for use in DNA amplification are stable, have a low error rate, and can be produced at a commercially reasonable cost. EBVpol and the modified EBVpol of this invention are more resistant to high ionic strength than the Φ29 DNA polymerase and is significantly less error-prone than BstI DNA polymerase.

This invention also provides methods for isothermal strand displacement DNA amplification using EBV DNA polymerase, including the modified EBVpol of this invention. The isothermal DNA amplification methods include, for example, multiple strand displacement amplification ("MSDA"), loop-mediated isothermal amplification ("LAMP"), rolling circle amplification ("RCA"), and multiple annealing and loop-based amplification cycles ("MALBAC"). These amplification methods can be applied to WGA using EBVpol and/or variants of EBVpol.

This invention also provides a method for amplifying a target nucleic acid sequence in vitro, the method comprising, (a) mixing a set of primers with a target nucleic acid sample sequence and incubating the primer-target sample mixture under conditions that promote and/or optimize amplification of the target nucleic acid sequence in step (b) below; (b) mixing an EBV DNA polymerase, including the wild-type EBVPol or any one of the modified EBV DNA polymerase of this invention, to produce a polymerase-primer-target sample mixture and incubating the polymerase-primer-target sample mixture under conditions that promote and/or optimize replication of the target sequence, wherein replication of the target sequence results in replicated strands, wherein during replication at least one of the replicated strands is displaced from the target sequence by strand displacement replication of another replicated strand. Thus, the target sequence is amplified. In certain embodiments, step (b) further comprises incubating the polymerase-target sample mixture under conditions that promote strand displacement. An EBV DNApol as defined herein includes wild-type EBVpol, variants thereof (including those of this invention), fragments thereof, and fusion proteins comprising EBV DNApol or a fragment or a variant thereof (including those of this invention). In certain further embodiments, the conditions that promote strand displacement comprise relatively high ionic strength. In yet certain further embodiments, the conditions that promote strand displacement comprise a concentration of a salt of about 60 mM to about 160 mM, and any concentration in between; the salt includes, for example, KCl, NaCl, ammonium sulfate or other monovalent salt, at, for example, a concentration of about 60 mM to about 160 mM, and any concentration in between, including about 80 mM to about 120 mM, about 100 mM. In other further embodiments, the conditions that promote strand displacement comprise a concentration of an acceptable salt that provides an ionic strength about equivalent to that of the conditions that promote strand displacement comprising a concentration of a salt of about 60 mM to about 160 mM, and any concentration in between; the salt includes, for example, KCl, NaCl, ammonium sulfate or other monovalent salt, at, for example, a concentration of about 60 mM to about 160 mM, and any concentration in between, including about 80 mM to about 120 mM, about 100 mM. In certain further embodiments, the conditions that promote and/or optimize replication of the target sequence are essentially isothermal; in even further embodiments, the temperature during step (a) and/or (b) is about 10° C. to about 65° C., and any temperature in between, including about 15° C. to about 45° C., about 20° C. to about 40° C. and about 20° C. to about 30° C., and any temperature in between any of these ranges. In yet further embodiments, neither step (a) nor step (b) involves thermal cycling. In certain embodiments, the target nucleic acid sample sequence is a sample of genomic nucleic acid and the genomic nucleic acid sample is from a prokaryote or a eukaryote (including human). The nucleic acid can be any nucleic acid. In certain embodiments, the nucleic acid is DNA. In certain other embodiments, the nucleic acid is RNA. The target nucleic acid sample can be obtained from any suitable source, including from a subject, including a human subject. A method of this invention can be applied to isothermal DNA amplification method, including, for example, multiple strand displacement amplification ("MSDA"), loop-mediated isothermal amplification ("LAMP"), rolling circle amplification ("RCA"), and multiple annealing and loop-based amplification cycles ("MALBAC").

Amplification methods of this invention using EBVpol, including the modified EBVpol of this invention, generally require a smaller number of repetitive DNA sequencing cycles to reach a target level of DNA amplification. As a result, these methods have a greater fidelity than current methods using Φ29 and BstI DNA polymerases. This greater fidelity results in a reduction in the number of repetitive DNA sequencing cycles that need to be performed to obtain statistically relevant sequence information, resulting in reduced processing time and reduced cost.

The amplified DNA resulting from the methods of this invention can then be used for any suitable applications; the amplified DNA, for example, can be subjected to DNA sequencing, to be cloned, to be further analyzed.

The exonuclease of EBVpol is required for low error rate and can be mutagenized to further lower the error rate or to increase processivity. In other aspects, this invention provides a method to increase the fidelity or the processivity of an EBV DNA polymerase, comprising: (a) mutagenizing the BALF5 subunit in its 3'-5' exonuclease domain (around residue 286 to around residue 555); (b) performing an isothermal DNA amplification on a known DNA sample with an EBV DNA polymerase comprising either a BALF5 mutant from step (a) or a wild-type EBV DNA polymerase; (c) obtaining results on the fidelity or the proccessivity of each of the EBV DNA polymerase tested; and (d) identifying the EBV DNA polymerase comprising a BALF5 mutant with increased fidelity or processivity than the wild-type EBV DNA polymerase.

This invention also provides kits comprising an EBV DNA polymerase, including a modified EBV DNA polymerase of this invention—both research-use only kits and diagnostic kits, including kits for point-of-service clinical assays in medicine, veterinary care, or agriculture. This invention thus provides kits comprising an EBV DNA polymerase, including a modified EBVpol of this invention, for use in isothermal DNA amplification. In certain further embodiments, the kit further comprises selected primers. In yet certain further embodiments, the selected primers of the kit comprise random sets of primers. In certain embodiments, the isothermal DNA amplification includes, for example and without limitation, multiple strand displacement amplification ("MSDA"), loop-mediated isothermal amplification ("LAMP"), rolling circle amplification ("RCA"), and multiple annealing and loop-based amplification cycles ("MALBAC").

Another application resulting from the amplified DNA from using the methods of this invention is nanopore sequencing. Nanopore DNA sequencing is an evolving technology for DNA sequencing that makes use of strand-displacing polymerase that is tethered to a membrane channel protein complex such that, as the polymerase copies DNA, the DNA is injected into the membrane channel. The electrostatic membrane potential is disturbed by the presence of DNA in the channel and the disturbance can be correlated with the actual sequence of the DNA in the channel. Stated another way nanopore DNA sequencing is based on "threading" DNA through a microscopic pore in a membrane. Specific nucleotide bases are identified by the way they influence ions flowing through the pore from one side of the membrane to the other. In yet other aspects, this invention provides using an EBV DNA polymerase, including any one of the modified EBV DNA polymerases of this invention, in nanopore DNA sequencing, wherein the DNA polymerase is tethered to a membrane channel protein complex. The membrane channel protein complex is any suitable membrane channel protein complex.

This invention also provides using an EBV DNA polymerase, including any one of the modified EBV DNA polymerases of this invention, in isothermal DNA amplification.

In further embodiments, the isothermal DNA amplification includes, for example and without limitation, MSDA, LAMP, RCA, MDA, or MALBAC.

The amplified DNA obtained from the methods of this invention are useful in a large number of applications, one of which is whole genome sequencing.

The advance of genomic medicine is coupled to progress in next-generation sequencing techniques, with the recent development of whole-genome sequencing of single cells. These methods rely on the whole genome amplification ("WGA") of a single cell's DNA to generate enough DNA for sequencing. However, WGA methods are prone to amplification bias which leads to inadequate genome coverage. PCR-based exponential WGA with random primers introduces sequence-dependent bias. Multiple-displacement isothermal WGA (also called multiple displacement amplification, or MDA) using the strand-displacing Φ29 DNA polymerase represents an improvement, but also introduces considerable bias due to nonlinear amplification. Recently, a new WGA method was reported: multiple annealing and loop-based amplification cycles ("MALBAC"), which introduces quasilinear preamplification to reduce the bias associate with nonlinear amplification. See Zong, C., et al., Science, 2012, 338(6114): p. 1622-6; Lu, S., et al., Science, 2012, 338(6114): p. 1627-30. MALBAC relies on the BstI DNA polymerase for the non-exponential phase of amplification, along with high-fidelity PCR enzymes for subsequent exponential amplification. With this method 85% genome coverage can be consistently obtained, with the best results being 93%, whereas in the same study, MDA provided 72% consistent genome coverage at comparable sequencing depth. This invention provides a method of using EBVpol, including the variants thereof of this invention, for use in WGA, instead of the BST DNApol.

The objective of single-cell genomic sequencing is the detection of single nucleotide variations ("SNVs") and copy-number variations ("CNVs") in cells to detect genetic changes that drive malignant cell behavior along with clinical outcomes, prenatal testing of several types, and forensic analysis, etc. Currently, for the best WGA technology, the most complete genome coverage that can be consistently achieved is 85-93%, so a considerable fraction of the potential SNVs is missed. Also, the enzyme used to copy the DNA is error prone, so the copying process itself can introduce variants that were not present in the cell. To sort out false positives, it is necessary to compare individually sequenced genomes from several closely related cells.

The problem of amplification bias in WGA for genomic sequencing significantly limits the usefulness of the technique, and it is mainly due to the idiosyncrasies of the enzymes used for amplification. BstI DNA polymerase functions at a high temperature (60° C.) and is relatively error prone, while Φ29 DNA polymerase functions best at 30° C. and is reportedly less error prone. For many isothermal amplification applications using these enzymes, primer design, temperature, ionic strength, and other reaction conditions are dictated by the properties of the enzymes, and a person skilled in the art can design the appropriate primers in each situation.

Some of the desirable properties of a DNA polymerase for DNA amplification, including for WGA, are: ease of obtainment, high specific activity, high processivity, high strand displacement activity, low mis-incorporation rate, high temperature optimum, functional at ambient temperature optimum, thermolability, and salt-tolerance. EBVpol and the modified EBVpol of this invention have most if not all of these properties.

Instead of heat denaturation, most isothermal techniques rely on the strand displacement activity of a DNA polymerase for strand separation of dsDNA. This particular property of some DNA polymerases, the ability to displace a DNA strand upstream of the primer-template junction, is unusual, even among enzymes that are highly processive. A high level of intrinsic SDA is uncommon among DNA polymerases. Those that have high level SDA include the Φ29 DNA polymerase, the BstI DNA polymerase large fragment, and the EBV DNA polymerase and the modified EBVpol of this invention.

In certain aspects, this invention provides methods using EBVpol as a commercial reagent for isothermal DNA amplification applications including but not limited to: point-of-service nucleic acid based diagnostics for infectious diseases, such as TB, HIV, malaria, leishmania, and sleeping sickness; whole-genome amplification for genomic sequencing for prenatal genetic testing; whole-genome amplification for genomic sequencing for cancer cell analysis; bacterial genomic sequencing for speciation and resistance testing; bacterial genomic sequencing for detection of food-borne contaminants; pathogen genomic sequencing for detection identification of potential bioterrorism agents; detection of genetically modified agricultural crops, detection of organisms in environmental samples in petrochemical exploration; detection of organisms in environmental samples for ecological research; detection of plant pathogens in the field; detection of animal pathogens in veterinary medicine; speciation of fish and other seafood in commercial seafood markets; and detection in the field of epidemic pathogens such as Ebola virus in establishing quarantine procedures in epidemics.

In other aspects, this invention provides a method for diagnosing a disease having an aberrant DNA (or nucleic acid) in a cell in a subject, comprising:
(a) isolating DNA from one or more cells of the subject;
(b) subjecting the DNA to DNA amplification in vitro using a method of this invention; and
(c) determining whether the subject's DNA is aberrant by, for example, DNA sequencing, the aberrant DNA being indicative of the disease.

The disease can be any disease that involves an aberrant DNA or RNA in a cell in the subject, including, for example, cancer, etc. The subject can be any subject, including a mammal, a human, etc.

This invention also provides methods and reagents for RNA expression profiling, which is carried out by first creating a cDNA (Complementary DNA) library of all the RNAs to be sequenced. This is usually carried out with the enzyme reverse transcriptase. Once the cDNA library, or pool, has been created at the single copy level, it must be amplified in order to be sequenced efficiently. That amplification is, at the practical level, quite similar to whole genome amplification, except the RNA corresponds to the "transcriptome," and not the entire genome. The transcriptome is about one-tenth of the whole genome, depending on the species and cell type.

In other aspects, this invention provides a method for profiling mRNA expression in a cell from a subject, comprising:
(a) isolating mRNA molecules from one or more cells of the subject;
(b) converting the mRNA molecules to cDNA molecules with reverse transcriptase;
(c) subjecting the cDNA molecules to amplification in vitro using a method of this invention, and
(d) quantifying the relative amount of one or more cDNA molecules, thus determining the expression levels of the corresponding mRNA molecules.

The subject can be any subject, including a mammal, a human, etc. The RNA profiling can be done for any reason that RNA profiling is needed.

The methods of this invention can be advantageously used for DNA amplification for a number of different purposes, for example, for diagnosis of infectious diseases, for whole-genome sequencing, for prenatal diagnosis, or for analysis of cancer cell genomes. The reagents, compositions, methods and kits of this invention can meet a number of needs. The market for gene-based testing represents the most rapidly expanding segment of the molecular diagnostics market. Gene-based tests are used in various industries including, for example, healthcare, agriculture (e.g., for detecting plant and animal diseases), and food testing. There is an increasing need to test using smaller and smaller volumes of tissues and blood; to test using simple sample collection methods for home testing (such as saliva and cheek swabs); prenatal single cell screening for a variety of developmental and neurological genetic disorders or diseases; and for cancers of high mortality where early detection in a heterologous tissue sample or blood is critical. Advances in science have allowed more accurate prediction of the probabilities for occurrence of diseases, and gene-based tests are used in tailoring personalized medicine for specific patient populations.

In certain embodiments, a method is provided for diagnosis, detection, and/or treatment of a subject, comprising: providing an amplified nucleic acid sequence using a method of this invention; using the amplified nucleic acid sequence for diagnosis, detection, and/or treatment for the following: point-of-service nucleic acid based diagnostics for infectious diseases, including TB, HIV, malaria, leishmania, or sleeping sickness; whole-genome amplification for genomic sequencing for prenatal genetic testing; whole-genome amplification for genomic sequencing for cancer cell analysis; bacterial genomic sequencing for speciation and resistance testing; bacterial genomic sequencing for detection of food-borne contaminants; pathogen genomic sequencing for detection and identification of potential bioterrorism agents; detection of genetically modified agricultural crops, detection of organisms in environmental samples in petrochemical exploration; detection of organisms in environmental samples for ecological research; detection of plant pathogens in the field, detection of animal pathogens in veterinary medicine, speciation of fish and other seafood in commercial seafood markets; or detection in the field of epidemic pathogens, including detection of Ebola virus, in establishing quarantine procedures in epidemics. The subject can be any subject, including a human subject. These methods are known in the field.

Methods and kits of use of the EBV DNA polymerase in isothermal amplification comprise selection of appropriate corresponding primer sets to optimize fidelity and process efficiency. Such primer sets can comprise primer sets currently in use for WGA.

Regarding primer design for the methods and kits of this invention, sequence preference is an important characteristic, since sequence is a major determinant of melting temperature and the degree to which ionic strength (salt concentration) affects the annealing. In certain embodiments, the primer sets described in U.S. Pat. No. 6,124,120 (the disclosure of which is hereby incorporated by reference in its entirety for all purposes) are used with advantage with EBVpol and its variants of this invention. Briefly, the primers can be oligonucleotides comprising a sequence complementary to the target nucleic acid sequence, and that sequence complementary to the target nucleic acid sequence on the primers can be any length supporting specific and stable hybridization between the primer and the target sequence (between about 10 to about 35 nucleotides long, and anything in between; and between about 16 to about 24 nucleotides long, and anything in between). For whole genome amplification, the sequence complementary to the target sequence can be between about 12 to about 60 nucleotides long, and anything in between. In certain further embodiments, the primers comprise additional sequence at the 5' end of the primer not complementary to the target nucleic acid sequence. This non-complementary portion of the primer can also include a functional sequence such as a promoter for an RNA polymerase. This non-complementary portion of a primer can be any length, including about 1 to about 100 nucleotides long, and anything in between; and can be about 4 to about 8 nucleotides long, and anything in between. In certain embodiments, in the case of multiple strand displacement amplification, the complementary portion to the target sequence of each primer is designed to be complementary to the hybridization target in the target sequence. In certain further embodiments, in a set of primers, the complementary portion of each primer can be complementary to a different portion of the target sequence. In certain further embodiments, the primers in the set can be complementary to adjacent sites in the target sequence.

In other embodiments, the "rules" for primer design for EBVpol are based on and adapted from those known in the field.

In other embodiments, an antibody, an aptamer, or a cross-linking reagent directed against either subunit of the EBVpol or its variants of this invention serves to tether the complex to a solid or colloidal matrix. Such a tethering agent is useful in developing kits for nucleic acid detection, especially for point-of-service clinical assays in medicine, veterinary care, or agriculture. Such tethered versions of EBVpol are also useful to stabilize the enzyme to reconstitute assay kits at the time of use. In a still further embodiment, some degree of tethering, if conditional or reversible, may be used to store the enzyme in a stable but inactive form, such as is used for "hot start" PCR enzymes. Antibodies and aptamers can be engineered to bind to EBVpol to inactivate it at temperatures below the isothermal amplification assay temperature, and to fall off EBVpol when the reaction vessel reaches a desired assay temperature. This approach provides the capability to avoid undesirable amplification side-reactions occurring at lower temperatures. Such antibody, aptamer, and cross-linking reagent are made by methods known in the art.

The methods of this invention can amplify nucleic acid samples containing 10 ng DNA or less, and can further amplify the DNA of such samples to provide at least about 2 μg to about 10 μg DNA, and any amount in between.

This invention provides a salt-tolerant EBV DNA polymerase, including the modified EBVpol of this invention, which is advantageous, at least in part because impurities introduced into amplification reactions from impure DNA samples tend to include salts which can inhibit other polymerases. In certain method embodiments, it can be desirable to have low salt, and in certain method embodiments, high salt. This can be determined by which primer sets are selected, the nature of the sample to be amplified, and the reaction conditions or, possibly, the length of time the assay will be run, etc. Therefore, having flexibility in the ability to "dial" the salt optimum one desires when one designs an isothermal amplification application is highly desirable. Different salt conditions will alter the way in which different primers anneal to different templates.

Nucleic Acid Amplification

The methods of this invention can make use of any suitable method for nucleic acid amplification, including an isothermal DNA amplification method, including, for example, multiple strand displacement amplification ("MSDA"), loop-mediated isothermal amplification ("LAMP"), rolling circle amplification ("RCA"), and multiple annealing and loop-based amplification cycles ("MALBAC"), using an EBVpol or a variant thereof of this invention. These known methods have not made use of EBVpol or its variants. The methods of this invention include using EBVpol or a variant thereof of this invention in these isothermal DNA amplification methods.

The most common use of DNA polymerases in biotechnology and medicine involves polymerase chain reaction ("PCR"). The first thermostable DNA polymerases (such as Taq) used for PCR were mostly family A enzymes obtained from thermophilic bacteria found in hot springs. These first-generation enzymes have low processivity and high misincorporation rates, on the order of $10^{-5}$, making the introduction of errors due to amplification a significant problem in cloning sequences larger than 10 kb. Subsequently, the so-called "vent" polymerases were introduced, which were family B polymerases obtained from deep-sea vent thermophiles or archaea. These enzymes exhibited greater fidelity, in the range of $10^{-6}$ due to their intrinsic 3'-5' exonuclease, or "proofreading" activity; however, there is a relative reduction in the incorporation rates, leading to somewhat reduced yields.

More recently, engineered forms of several thermostable polymerases have appeared in which a DNA-binding or processivity-increasing domain, such as the small thermostable protein Sso7d from *Sulfolobus solfactaricus*, has been fused genetically to the polymerase, with roughly ten-fold increases in fidelity and modestly increased processivity. Others have devised different strategies for engineering DNA polymerase by combining heterologous catalytic and DNA binding domains. Presently, the best fidelity that can be obtained with a thermostable enzyme suitable for PCR is roughly $10^{-7}$, or 100-200 times better than the prototypical Taq polymerase.

Several alternative methods for amplifying DNA without thermocycling, i.e., isothermally, have been developed, which may be carried out with less sophisticated requirements for thermal control, such as heat blocks, water baths, or carried out even at ambient temperature, with simplified detection methods such as turbidity (Mori, Y., et al., *Biochem Biophys Res Commun*, 2001, 289(1): p. 150-4; Tomita, N., et al., *Nat Protoc*, 2008, 3(5): p. 877-82). Since thermocyclers are generally expensive, isothermal DNA amplification, especially if carried out at ambient temperature, is advantageous. These methods can be performed using EBVpol and its variants of this invention. These methods are publicly available and are known to a person of ordinary skill in the art; and these methods can be adapted to use an EBVpol, including a modified EBVpol of this invention.

An example of an isothermal DNA amplification procedure involves the use of a "bump" primer for strand displacement and a nicking activity (Takahashi, H., et al., *Biotechniques*, 2009, 47(1): p. 609-15). This method is a form of MSDA. See, e.g., New England BioLabs (NEBioLabs, Ipswich, Mass.) commercial literature 2012: "Improved reagents for isothermal DNA amplification." This method can be performed using EBVpol and its variants of this invention. This method is publicly available and is known to a person of ordinary skill in the art; and this method can be adapted to use an EBVpol, including a modified EBVpol of this invention.

Isothermal DNA amplification procedures that make use of primers can employ some agent or process that can separate the primer and the nascent DNA strand from the template for the amplification to proceed. Various strategies have been developed for isothermal DNA amplification which involve the use of sets of nested primers that allow for multiple priming events to occur in both directions within a target DNA sequence, along with sequential displacement of primers with or without formation of loops. Unlike PCR, the products of isothermal DNA amplification, such as in rolling circle amplification (see, e.g., Dean, F. B., et al., *Genome Res*, 2001, 11(6): p. 1095-9), are quite heterogeneous, complex in structure, and difficult to analyze. Instead of heat denaturation, most isothermal techniques rely on the strand displacement activity of a DNA polymerase for strand separation of dsDNA.

An application of strand displacement activity is RCA, which currently allows for 10,000-fold amplification of DNA using random hexamer primers in several hours at 30° C. using Φ29 DNA polymerase, copying DNA >70 kb in length (Dean, F. B., et al., *Genome Res*, 2001, 11(6): p. 1095-9; Lizardi, P. M., et al., *Nat Genet*, 1998 19(3): p. 225-32). Until now, the error rate of Φ29 DNA polymerase makes this method only suitable for the amplification of small genomes, such as viruses, plasmids, mitochondria, and smaller bacterial genomes. Briefly, oligonucleotide primers complementary to the amplification target circle are hybridized to the circle. The addition of DNA polymerase and deoxynucleoside triphosphates (dNTPs) to the primed circle results in the extension of each primer, and displacement of each newly synthesized strand results from elongation of the primer behind it. Secondary priming events can subsequently occur on the displaced product strands of the initial rolling circle amplification step. This method can be performed using EBVpol and its variants of this invention. This method is publicly available and is known to a person of ordinary skill in the art; and this method can be adapted to use an EBVpol, including a modified EBVpol of this invention.

LAMP is an isothermal DNA amplification method that uses four core primers (FIB, BIP, F3, and B3) recognizing six distinct sequence regions on the target, with two primers containing complementary sequence in order to create loop structures that facilitate exponential amplification (Notomi, T., et al., *Nucleic Acids Res*, 2000, 28(12): p. E63). LAMP was developed using BstI DNA polymerase large fragment, with an optimum temperature of 65° C. Sequential binding of inner and outer primers is necessary for propagation of the amplification reaction (Notomi, T., et al., *Nucleic Acids Res*, 2000, 28(12): p. E63; Tomita, N., et al., *Nat Protoc*, 2008, 3(5): p. 877-82). LAMP may be used for simultaneous multiple target detection in real-time using a quenched-fluorophore detection method and BstI DNA polymerase (Tanner, N. A., et al., *Biotechniques*, 2012, 53(2): p. 81-9). This method can be performed using EBVpol and its variants of this invention. This method is publicly available and is known to a person of ordinary skill in the art; and this method can be adapted to use an EBVpol, including a modified EBVpol of this invention.

Multiply-primed rolling circle amplification using random hexamer primers was developed with the Φ29 DNA polymerase, which has high processivity, high fidelity due to its "proofreading" 3'-5' exonuclease activity, and significant strand displacement activity. Furthermore, although not thermostable for PCR, the Φ29 DNA polymerase has a broad operational temperature range, extending down into typical room temperatures, allowing reactions to be carried out at ambient temperature. Recently, through protein domain "swapping and tagging," the Φ29 DNA polymerase has been engineered for increased processivity that results in an improved efficiency of amplification. This method can be performed using EBVpol and its variants of this invention. This method is publicly available and is known to a person of ordinary skill in the art; and this method can be adapted to use an EBVpol, including a modified EBVpol of this invention.

MSDA has been used for human genomic sequencing with significantly less amplification bias than PCR (Dean, F. B., et al., *Proc Natl Acad Sci USA*, 2002, 99(8): p. 5261-6). In detecting single nucleotide changes (or single nucleotide polymorphisms—SNPs) in a haploid human genome of $3 \times 10^9$ nucleotides, the introduction of errors by the amplification method can be a huge problem. One way that random copying errors may be distinguished from true single nucleotide point mutations is by multiple rounds of sequencing amplified DNA to determine which single nucleotide point changes occur constantly in each "read" and which ones occur randomly. This method is publicly available and is known to a person of ordinary skill in the art; and this method can be adapted to use an EBVpol, including a modified EBVpol of this invention.

The number of multiple "reads" necessary to confirm a particular SNP is dependent on the error rate of the amplification process. Therefore, the efficiency of whole genome amplification for genomic sequencing is linked to the fidelity of the amplification prior to sequencing. The use of an enzyme such as Taq polymerase, with a misincorporation rate of 10–5, would introduce $10^{-4}$ errors that would have to be distinguished from true SNPs by a computationally intensive analysis, one that would tax the state-of-the-art bioinformatics capabilities. Alternatively, an amplifying enzyme such as Φ29 DNA polymerase, which possesses a 3'-5' proofreading exonuclease, has a misincorporation rate of $10^{-6}$ to 10–7, which provides acceptable fidelity for whole genome amplification. However, any further improvement in fidelity of the amplification prior to sequencing will further reduce the requirement for multiple sequencing "reads" in order to sort mis-incorporation errors from true SNPs.

Recently, a new WGA method was reported: multiple annealing and loop-based amplification cycles ("MAL-BAC"), which introduces quasilinear preamplification to reduce the bias associate with nonlinear amplification. See Zong, C., et al., *Science*, 2012, 338(6114): p. 1622-6; Lu, S., et al., *Science*, 2012, 338(6114): p. 1627-30. MALBAC relies on the BstI DNA polymerase for the non-exponential phase of amplification, along with high-fidelity PCR enzymes for subsequent exponential amplification. This method is publicly available and is known to a person of ordinary skill in the art; and this method can be adapted to use an EBVpol, including a modified EBVpol of this invention.

Because of DNA repair mechanisms, fewer than a single nucleotide change per $10^9$ nucleotides are introduced during human DNA replication. The fidelity of DNA replicative machinery in vivo, apart from repair, expressed as the average single nucleotide misincorporation rate, is approximately $10^{-7}$ to $10^{-8}$. Part of this fidelity is due to the presence of a proofreading 3'-5' exonuclease in all replicative complexes that contributes at least a factor of $10^{-2}$, which can be removed through mutational alteration of the 3'-5' exonuclease domains of replicative DNA polymerases. Therefore, the misincorporation rate of the catalytic site of nucleotide addition is considerably higher than is reflected in the overall result of DNA replication in vivo.

In certain embodiments, The compound known as "betaine," and the like, is used in an amplification reaction of a method of this invention to manipulate the melting temperatures of target-specific primers. Many amplification protocols, especially those employing BstI DNA polymerase, include betaine and other such compounds for establishing optimum conditions for amplification.

All of the above-described methods of isothermal DNA amplification are known to a person of ordinary skill in the art; and these methods can be adapted to use an EBVpol, including a modified EBVpol of this invention.

EXAMPLES

For this invention to be better understood, the following examples are set forth. These examples are for purposes of illustration only and are not be construed as limiting the scope of the invention in any manner.

Example 1. Purification of BALF5 and BMRF1 Expressed in Insect Cells by Recombinant Baculoviruses From p19-BMRF1 (Kiehl, A. and D. I. Dorsky, *Virology*, 1991, 184(1): p. 330-40. Kiehl, A. and D. I. Dorsky, *J Virol*, 1995, 69(3): p. 1669-77), a BclI-EcoRI fragment containing the BMRF1 open reading frame was inserted into the pEVmXIV transplacement vector, downstream from the PXIV promoter, which is more powerful than the conventional Ppolh promoter (Baculovirus Expression Vector Manual by Lois K. Miller, 1993) to obtain pEV-M2, in which the BMRF1 translational initiator is 5 base pairs from the insertion site.

The BALF5 open reading frame ("ORF") was mobilized on a HindIII-XbaI fragment of pYEX-X2 (Kiehl, A. and D. I. Dorsky, *Virology*, 1991, 184(1): p. 330-40. Kiehl, A. and D. I. Dorsky, *J Virol*, 1995, 69(3): p. 1669-77), blunt-ended with Klenow enzyme, and inserted into pEVmXIV, with the proper orientation selected and verified by restriction mapping. In the resulting plasmid, pEV-X2, the BALF5 translational initiator is 10 base pairs from the insertion site.

Recombinant baculoviruses expressing BMRF1 and BALF5 were constructed as described (Baculovirus Expression Vector Manual by Lois K. Miller, 1993). Separate cultures of Sf9 insect cells were transfected with the baculovirus transplacement vectors pEV-M2 and pEV-X2 combined with linearized wild-type AcNPV baculovirus (InVitrogen, Carlsbad, Calif.). The viral outputs from the transfections were titered by plaque assay on Sf9 monolayers. Ten recombinant virus plaques (lacking wild-type inclusion bodies) for each transplacement vector were picked and carried through three cycles of plaque-purification on Sf9 monolayers. Four recombinant viruses expressing EBV BMRF1 were identified by immunofluorescence microscopy of infected Sf9 cells, and one expressing BALF5 was identified by SDS-PAGE, and high-titer stocks were prepared from the recombinant baculoviruses on Sf9 cells, following three-stage plaque purification. Insect tissue culture cells were infected with the high-titer stocks of pAc-BALF5 and pAc-BMRF1 and cell extracts prepared 72 hours post-infection ("hpi") were analyzed by SDS-PAGE and Coomassie blue staining, showing the appearance of the recombinant 110 kDa BALF5 and 50 kDa BMRF1 products. Large quantities of both BALF5 and BMRF1 were also expressed at 40 hpi, although more of the BMRF1 material was extractable. Also, the insect cell-expressed BMRF1 was identified by immunoblotting.

Sf9 cells infected with pAc-BALF5 at a multiplicity of 20 were harvested at 40 hpi into 50 mM Tris-HCl pH 8.0, 1 mM EDTA, 20% (w/v) glycerol, 1 mM PMSF, sonicated briefly, and centrifuged. The pellet, containing most of the BALF5, was then sonicated in the same buffer containing 2M KCl, and centrifuged. The low-salt extraction removed nearly all of the baculovirus and Sf9 DNA polymerase activity. The 2M KCl extract contained more than 50% of the expressed BALF5 and was nearly homogeneous on SDS-PAGE. The 2M KCl extract was dialyzed to 100 mM KCl and chromatographed on phosphocellulose, eluted with a 0.1-0.8 M KCl gradient. The eluted fractions were assayed for DNA polymerase activity at high and low ionic strength. A large peak of low ionic strength activity eluted at about 0.3 M KCl, which lacked activity at high ionic strength. SDS-PAGE analysis showed that the peak material was a 110 kDa polypeptide. The phosphocellulose-purified BALF5 was further purified by heparin-agarose chromatography, eluting at 250 mM NaCl.

The baculovirus-expressed BMRF1 was purified from pAc-BMRF1 infected Sf9 cells at 48 hpi. Whole-cell sonicates prepared in 50 mM Tris-HCl pH 8.0, 1 mM EDTA, 20% (w/v) glycerol, 1 mM PMSF, centrifuged, and re-sonicated in the same buffer containing 1 M KCl. Monitored by immunoblot, the BMRF1 partitioned equally between low- and high-salt extraction buffers, but represented a much higher fraction of the total protein in the high-salt extraction. Therefore, the 1 M KCl-extractable BMRF1 was dialyzed against 0.1 M KCl and chromatographed on phosphocellulose, then heparin-agarose. Elution of BMRF1 was followed by immuno-dot-blotting of fractions with the MAB8186 Anti-EBV EA-D-p52/50 Antibody, clone R3 (EMD Millipore, division of Merck KGaA, Darmstadt, Germany). Purified BMRF1 and BALF5 were analyzed and confirmed by SDS-PAGE.

The purified BALF5 possessed significant DNA polymerase elongation activity on activated calf thymus ("CT") DNA at low ionic strength, but was completely inactive at 100 mM ammonium sulfate. When assayed in the presence of BMRF1, its activity on CT DNA at 100 mM ammonium sulfate was greater than 100-fold increased over its activity alone, in the absence of salt. At concentrations required for stimulation at high-salt, BMRF1 did not appear to significantly decrease the low-salt activity of BALF5. At high salt, the EBVpol activity was 60% inhibited by 20 mM PAA (phosphonoacetic acid, a well-described specific inhibitor of herpesvirus DNA polymerases which does not inhibit host-cell DNA polymerases).

Example 2. Reconstituted Recombinant EBV DNA Polymerase Holoenzyme, Composed of 1:1 Complex of BALF5 and BMRF1 (1-303)

Purified BALF5 protein is prepared from Sf9 insects cells bearing the Ac-BALF5 baculovirus vector, an expression plasmid vector bearing the full-length BALF5 gene. Purified BMRF1(1-303) is prepared from E. coli transformed with pGST-BMRF1(1-303), a expression plasmid vector bearing the GST-BMRF-1 (1-303) DNA. The proteins are purified and reconstituted.

The following assays are performed with the reconstituted recombinant EBV DNA polymerase holoenzyme, composed of 1:1 complex of BALF5 and BMRF1(1-303): DNA elongation, 3'-5' exonuclease, processivity, effect of ionic strength on activity, effect of standard inhibitors (PFA, aphicidolin, ACV-TP) on activity, exclusion of contaminating activities, 5' exonuclease activity, endonuclease activity, DNA helicase activity, and strand displacement activity. The following DNA amplification methods are performed with the reconstituted recombinant EBV DNA polymerase holoenzyme, composed of 1:1 complex of BALF5 and BMRF1(1-303): isothermal DNA amplification with random hexamer-primed rolling circle; isothermal DNA amplification using LAMP; WGA of E. coli bacterial genome with random hexamer primers; WGA of human DNA using MALBAC and the Φ29 protocol (Burtt, N. P., *Cold Spring Harb Protoc,* 2011, 2011(1): p. pdb prot5552). Next-generation sequencing of WGA to determine bias spectrum is also performed using the reconstituted recombinant EBV DNA polymerase holoenzyme, composed of 1:1 complex of BALF5 and BMRF1(1-303). Comparison of 029, BstI, and EBV DNA polymerase in WGA are also performed using the EBV DNA polymerase holoenzyme, composed of 1:1 complex of BALF5 and BMRF1(1-303).

Example 3. Engineering of BALF5

A. Affinity Tag

The baculovirus vector comprising the BALF5 gene is engineered so that the gene is fused with an affinity tag, such as 6×-his (SEQ ID NO. 7) or MBP. For example, a baculovirus vector comprises BALF5 fused with a carboxyl-terminal MBP or 6×-his tag (SEQ ID NO. 7). Such a fusion protein could achieve higher levels of expression and will allow rapid affinity purification of recombinant BALF5.

B. Prokaryotic Expression of BALF5

When expressed in E. coli, the BALF5 polypeptide is insoluble and forms inclusion bodies that are resistant to refolding methods that are successful for many other proteins. To achieve expression of properly folded BALF5 in E. coli, E. coli strains expressing the human Hsp90R are used. Prokaryotic BALF5 expression plasmids are inserted into E. coli strains expressing one or more of several known folding chaperones, including Hsp90. Soluble recombinant BALF5 proteins obtained from these expression systems are purified by anion exchange and heparin affinity chromatography and assayed for catalytic activity. The expression plasmid can be engineered to include 6×-his (SEQ ID NO. 7) or MBP affinity purification tags on the BALF5 protein.

Recently published work has shown that phosphorylation of threonine 178 in BALF5 is necessary for interaction with the prolyl-isomerase Pin1, which is necessary for EBV DNA replication, suggesting that proline isomerization is somehow necessary for correct folding of BALF5. Therefore, systematic mutagenesis of BALF5 proline residues is carried out, with special attention to the region around threonine 178, and additional mutations are introduced around threonine 178 to allow correct folding of the bacterially expressed BALF5 protein.

C. Mutagenize the 3'-5' Exonuclease Domain

The BALF5 gene is mutagenized in the 3'-5' exonuclease domain to increase fidelity or to increase processivity. Residue 296 of BALF5 is mutagenized from D to A (D296A); residue 298 is mutated from E to A (E298A). A double mutant BALF5 comprising both mutations (D296A and E298A) is also constructed.

D. BALF5 Mutation with Increased Fidelity in DNA Amplification

A BALF5 mutant variant is constructed by standard recombinant DNA techniques. This mutant variant comprises the region I GDTDS (SEQ ID NO. 4) mutated to GDTDA (SEQ ID NO. 5), with the S to A mutation being at residue 765 of BALF5 (S765A). This mutant EBVpol BALF variant protein (comprising a S765A mutation) exhibits increased replication fidelity when compared to the wild type protein, when reconstituted as a holoenzyme with BMRF1.

E. Expression of BALF5 Polypeptide in Sf9 Insect Cells Using Ac-BALF5 Baculovirus Plaque isolates of Ac-BALF5 from samples were amplified and shown to induce a 110 kDa polypeptide in Sf9 cells, demonstrated by SDS-PAGE. High-titer viral lysates of Ac-BALF5 is prepared on Sf9 by standard methods and is used to infect large-scale Sf9 cultures for production of recombinant BALF5.

F. Purification of BALF5 Polypeptide Expressed in Sf9 Insect Cells

Methods for expressing and purifying the BALF5 catalytic subunit of EBV DNA polymerase from insect cells have been developed.

With the availability of newer insect cell lines, such as the Hi5 insect cell line derived from *Trichoplusia ni*, or such as BALF5 that can be obtained by infecting *Trichoplusia ni* (Cabbage Looper) fourth-instar larvae with the Ac-BALF5 virus and extracting the BALF5 from the infected larvae four days after infection, it may be possible to increase the yield of BALF5 polypeptide without re-engineering the expression vector. Therefore, available insect cell lines are screened for yield of BALF5 expression using the Ac-BALF5 baculovirus vector. The method for extracting BALF5 from Sf9 cells involves sonication and sequential low-salt and high-salt extractions, with the dialyzed high-salt extraction containing most of the BALF5 activity and relatively deficient in host cell and vector DNA polymerases, which are substantially extractable at low-salt. This method differs substantially from the method published by Tsurumi (Tsurumi, T., et al., *J Virol*, 1993, 67(8): p. 4651-8) and appears to represent a significant improvement in yield. The dialyzed high-salt extractable BALF5 is then purified in two stages: anion-exchange chromatography on high-performance Mono S columns, followed by heparin-affinity chromatography.

G. The Carboxyl Terminus of EBV BALF5 is Dispensable for Binding BMRF

To determine if the extreme carboxyl terminus of the EBV BALF5 subunit is necessary for functional interaction with BMRF1, a series of deletions of the BALF5 open reading frame was constructed in the pYES-X2 vector and [$^{35}$S]-methionine labeled polypeptides were expressed by in vitro transcription-translation as described (Kiehl, A. and D. I. Dorsky, *J Virol*, 1995, 69(3): p. 1669-77). These radiolabeled BALF5-deletion polypeptides were then assayed for binding to GST-BMRF1(1-303) in 100 mM ammonium sulfate. In vitro translated BALF5 bound to GST-BMRF1 (1-303) but not to GST alone. Deletion of the amino-terminal 160 residues of BALF5 ("N160") did not prevent binding to GST-BMRF1, nor did the internal deletion of residues 107-550 (A107-550). Deletion of the carboxyl terminal 465 residues ("C550") yielded a polypeptide that did not bind to GST-BMRF1(1-303), but binding was preserved in ΔC903, with a deletion of the carboxyl-terminal 112 residues of BALF5.

Furthermore, the BALF5 ΔC903 polypeptide showed wild-type DNA polymerase activity in vitro, with stimulation by the BMRF1 processivity factor, whereas the N160, C550 and A107-550 polypeptides were catalytically inactive with or without the addition of BMRF1 and at high and low ionic strength. Deletion of the extreme carboxyl-terminal 112 residues, therefore, preserved both physical binding and functional interaction between BALF5 and BMRF1, demonstrating a significant structural difference between the HSV and EBV DNA polymerases.

Example 4. Engineering of BMRF1

A. Linker Insertion Mutagenesis

The BMRF1 expression plasmid pYES2-M1 was pseudorandomly linearized with the frequently cutting enzyme HaeIII (27 sites in the BMRF1 ORF) in the presence of 1 mg/ml ethidium bromide (Kiehl, A. and D. I. Dorsky, *J Virol*, 1995, 69(3): p. 1669-77). The unit-length plasmid was gel-purified, treated with bacterial alkaline phosphatase, and ligated with an excess of the EcoRI linker 5' CCGGAAT-TCCGG (SEQ ID NO. 6), which had been 5' phosphorylated with T4 polynucleotide kinase. After digestion with EcoRI, the DNA was gel-purified, ligated with T4 DNA ligase at a DNA concentration of 0.01 mg/ml, and transformed into *E. coli* HB101. Ampicillin-resistant colonies were selected and DNA mini-preps were screened for EcoRI sensitivity (pYES2-M1 has no EcoRI sites). HindIII and BglII sites define the proximal and distal ends of the BMRF1 ORF, so plasmids containing the linker were subjected to triple digestion with EcoRI, HindIII, and BglII in order to map the insertions within the BMRF1 ORF. Insertions within BMRF1 were then mapped exactly by end-labeling small restriction fragments either containing the insertion site or having one EcoRI end and determining the length on a 6% sequencing gel, using a known sequence ladder for exact size determination. Insertion sites were then confirmed by direct DNA sequencing (Kiehl, A. and D. I. Dorsky, *J Virol*, 1995, 69(3): p. 1669-77). Linker insertion mutants were named for the BMRF1 codon which they altered.

B. Expression and Purification of GST-BMRF1(1-303) in *E. coli*

The BMRF1(1-303) polypeptide as a GST-fusion is advantageously expressed in *E. coli*. Improvement in protein yield can be accomplished by, for example, using readily-available *E. coli* strains with less-common bacterial tRNA genes such that the codon preferences of the eukaryotic GST-BMRF1(1-303) gene fusion do not limit protein expression; and, as a second example, inclusion of systems for expressing endogenous lysozymes that facilitate cell breakage and extraction of the recombinant GST-BMRF1 (1-303) polypeptide. Even without these improvements, large amounts of soluble GST-BMRF1(1-303) polypeptide can be obtained. Current methods allow for cell breakage without using harsh physical methods. Cell extracts can be effectively cleared of nucleic acids using Benzonase®, which has no protease activity.

Vectors were created that allowed expression of glutathione-S-transferase (GST)-BMRF1 fusion polypeptides under the control of the T7 promoter system in *E. coli* (Zhang, Q., et al., *J Gen Virol*, 1999, 80 (Pt 1): p. 69-74; Zhang, Q., et al., *Virology*, 1997, 230(1): p. 22-34; Zhang, Q., et al., *J Virol*, 1996, 70(8): p. 5131-42). The 0.7 kb Eco N1/Klenow blunted-Eco RI fragments containing the GST open reading frame were mobilized from the commercial vectors pGEX-2T and pGEX-3X (GE Healthcare Life Sciences, Pittsburgh, Pa.) and ligated with the Nhe I/Klenow blunted-Eco RI fragment of pGEMEX-1 (Promega, Madison, Wis.) containing the T7 promoter region, using the ampicillin selectable marker. These resulting vectors were named pT7-GEX-2T (thrombin GST cleavage site) and pT7-GEX-3X (factor Xa cleavage site), respectively. The BMRF1 (1-303) ORF was mobilized on a BclI-NotI/Klenow blunted fragment from p19-BMRF1 DNA prepared in a dam⁻ E. coli host and ligated into the pGEX-3X vector (GE Healthcare Life Sciences, Pittsburgh, Pa.) at the Bam HI and Eco RI/Klenow blunted sites to create the intermediate construct pGEX-2T-BMRF1(1-303). Then a 1.4 kb BstB I-Tth III I/Klenow blunted fragment from pGEX-2T-BMRF1(1-303) was ligated with 3.5 kb BstB I-Eco RI/Klenow blunted fragments of pT7-GEX-2T and pT7-GEX-3X, respectively. The resulting vectors were named pGST-BMRF1(1-303)-2T and pGST-BMRF1(1-303)-3X, respectively. BMRF1 mutations were mobilized from the pYES2-M1 mutant parent vectors on internal restriction fragments for ligation into the pGST-BMRF1(1-303) vectors.

The pGST-BMRF1(1-303) vectors were transformed into the E. coli strain BL21*pLysS, which has an IPTG-inducible T7 RNA polymerase gene. Transformed colonies were selected on ampicillin and chloramphenicol containing LB agar plates and used to inoculate overnight cultures of LB containing ampicillin and chloramphenicol. Expression was carried out by dilution of the overnight culture 1:10 into LB containing ampicillin and chloramphenicol, growing for three hours at 37° C. with shaking, then 80 micrograms per mL of solid isopropylthiogalactoside ("IPTG") were added, to induce T7 RNA polymerase expression, followed by another two hours of shaking at 37°. Bacteria were collected by centrifugation, resuspended in an equal weight of lysis buffer containing a protease inhibitor cocktail (Calbiochem, San Diego, Calif.), and cells were broken by sonication. Cell lysis supernatants were obtained by centrifugation at 5,000×g for 10 minutes at 4° C.

In another protocol, the GST-BMRF1(1-303) fusion polypeptide is purified from bacterial extracts by binding to glutathione-agarose which is stable to 1M NaCl and other relatively harsh washing conditions, allowing for highly-effective one-step affinity purification. Cleavage of the GST-BMRF1(1-303) fusion polypeptide is carried out on the affinity-resin bound form by the addition of the cleavage proteases thrombin or FXa (activated factor X). The cleaved BMRF1(1-303) polypeptide is then eluted from the affinity column, leaving the GST moiety bound. Both cleavage methods have been employed for the GST-BMRF1(1-303) fusion polypeptide and they appear to work equally well. Cost considerations are examined to determine which cleavage method to employ for commercial development.

Double-stranded DNA-cellulose affinity chromatography is used as the final step of purification of the BMRF1(1-303) polypeptide. The dsDNA-agarose affinity matrix is easily obtainable and can also be easily prepared using activated agarose beads and purified activated calf thymus DNA. The cleaved BMRF1(1-303) polypeptide binds the affinity matrix well and elutes conveniently at 300-500 mM NaCl, whereas the cleaved GST affinity tag does not bind to the affinity matrix and is easily separated. The affinity tag 6×-his (SEQ ID NO. 7) does not bind to dsDNA-agarose after cleavage either.

Different cleavage sites can be engineered into the GST-BMRF1(1-303) expression plasmid, allowing for using, for examples, enterokinase or PreScisson®.

C. GST-BMRF1 Fusion Binding to BALF5

A GST fusion with BMRF1 residues 1-303 was constructed and expressed in E. coli BL21*DE3 as a soluble 58 kDa protein which bound specifically to glutathione-agarose. Glutathione agarose beads were incubated in bacterial extract containing either 27 kDa wild-type GST or 58 kDa GST-BMRF1 and extensively washed in PBS, or 50 mM Tris-HCl, pH 8.0 containing 0, 50, 100, 150, or 200 mM ammonium sulfate. The beads were then incubated in the same wash buffers in the presence of [$^{35}$S]-methionine labeled in vitro translated BALF5, and then the beads were washed extensively at the same salt concentrations as the incubations. The washed beads were boiled in SDS sample buffer and the eluted proteins were analyzed by SDS-PAGE/fluorography. Measures taken to avoid the copurification of nucleic acids included washing the column at 600 mM NaCl and application of DNase to the column. And SDS-PAGE analysis was used to monitor GST-BMRF1 (1-303). In vitro translated BALF5 was shown to bind specifically to the GST-BMRF1 fusion and to bind poorly at 0 and 200 mM ammonium sulfate, but it bound efficiently in PBS and 50-150 mM ammonium sulfate. Non-specific binding of BALF5 to the 27 kDa GST was very weak and independent of salt concentration.

D. Deletion Mutagenesis of BMRF1

Carboxyl-terminal deletions of BMRF1 were constructed by digestion at unique restriction sites and a unique XbaI site distal to the BMRF1 ORF, filling in with Klenow enzyme, and religating (ΔC303 (1-303)-NotI, ΔC342 (1-342)-AvrII, and ΔC371 (1-371)-EcoRI of 1-371). ΔC279 (1-279) was obtained by digesting with AatII and NotI, treated with S1 nuclease, religating, and selecting the mutant from sequenced plasmids. ΔC303 is a deletion of the C-terminal 101 amino acids. Internal deletions were created by digestion at linker insertion sites and naturally occurring unique restriction sites, creating blunt ends with either Klenow enzyme or S1 nuclease when necessary, and religating. Restoration of reading frame by internal deletions was confirmed by dideoxy DNA sequencing and by demonstrating that the in vitro translated polypeptide specifically reacted with MAb 90E2, which recognizes an epitope at the carboxyl terminus of BMRF1, proving that the proper reading frame was established by the construction. Construction of internal deletions was carried out as shown in Table 1.

TABLE 1

| deletion Mutant (residues deleted) | Procedure for Construction | Sequence Alteration |
|---|---|---|
| Δ45-98 | Eco RI of 1-44/Klenow and EcoN1/Klenow | G44-RNC-K99 |
| Δ80-204 | Eco RI of 1-79/sticky and Eco RI of 1-205/sticky | A79-GIP-A205 |
| Δ124-217 | Eco RI of I-122/sticky and Eco RI of 1-217/sticky | P123-EFR-P218 |
| Δ194-217 | BspE I/Klenow and Eco RI of 1-217/Klenow | P193-EFR-P218 |
| Δ206-236 | Eco RI of 1-205/sticky and Eco RI of I-237/sticky | A205-AGIP-A237 |
| Δ218-233 | Eco RI of 1-217/Klenow and Eco RI of 1-234/Klenow | A217-GIP-A234 |
| Δ238-276 | Eco RI of I-237/sticky and Eco RI of 1-277/sticky | A237-GIP-A277 |
| Δ278-306 | Aat II/S1 and Not I/S1 | A277-A307 |
| Δ302-306 | Not I/S1 only | E201-A307 |
| Δ317-378 | Sma I and Nru I (both blunt) | R316-P-R379 |

E. BMRF1 Mutations that Affect Sensitivity of DNA Polymerase Activity to Ionic Strength Structure-activity studies of BMRF1 previously reported (Tsurumi, T., T. Daikoku, and Y. Nishiyama, J Virol, 1994, 68(5): p. 3354-63) showed that several internal deletions retained dsDNA binding activity but did not support BALF5 processivity at 100 mM ammonium sulfate, the ionic strength normally used to assay herpesvirus DNA polymerase activity. When assayed at lower ionic strength (50 mM ammonium sulfate), it was determined that several of the BMRF1 deletion mutants displayed significant activity as DNA polymerase accessory factors, as shown in Table 2.

TABLE 2

| Mutant | dsDNA-Binding | EBVPol Activity | |
|---|---|---|---|
| | | 100 mM | 50 mM (conc. (NH$_4$)$_2$SO$_4$) |
| WT (1-404) | + | + | − |
| ΔC303 | + | + | − |
| Δ124-217 | − | − | − |
| Δ194-217 | + | − | + |
| Δ206-236 | + | +/− | + |
| Δ205-217 | + | +/− | + |
| Δ206-236 | + | − | + |
| Δ218-233 | + | +/− | + |
| Δ238-276 | − | − | − |
| Δ278-306 | + | + | − |

The deletion mutations affecting sensitivity to high ionic strength are located within residues 194-236 of BMRF1. The crystal structure of EBV BMRF1 (Murayama, K., et al., *J Biol Chem*, 2009 284(51): p. 35896-905) identified two subdomains of similar folding topology, consistent with the prediction of a bipartite DNA-binding domain structure of BMRF1 (Kiehl, A. and D. I. Dorsky, *J Virol*, 1995, 69(3): p. 1669-77). These subdomains are residues 1-148 and 159-299 (αA2-βB2-βC2-βD2(loop)-βE2-βF2-αB2) with a 16-residue insertion (residues 213-228) between βD2 and βE3 in the C-terminal subdomain (Murayama, K., et al., *J Biol Chem*, 2009, 284(51): p. 35896-905). This region forms a loop structure which is stabilized by a hydrophobic interaction between Phe 222 and the protein core (Id.). Since this hydrophobic interaction between Phe 222 and the protein core appears to play an important role in the stability of the tertiary structure of BMRF1, this hydrophobic interaction can be further stabilized by high ionic strength and weakened by lower ionic strength.

Most DNA polymerases used for DNA amplification in the laboratory have optimum activity at low ionic strength, roughly the equivalent of 10-50 mM NaCl or (NH$_4$)$_2$SO$_4$. DNA polymerases that tolerate higher ionic strength offer several advantages. In sequencing or amplifying DNA with high GC content, fidelity can be increased by high ionic strength conditions. Also, in some situations, extraction of DNA samples may require the use of high salt concentrations, so amplification might require a de-salting step if the DNA polymerase used for subsequent amplification is salt-sensitive. Therefore, a salt-tolerant DNA polymerase is desirable, especially for some clinical diagnostic applications where the extraction of target samples leads to the introduction of salt into the amplification reaction.

These BMRF1 deletion mutants tolerant of low ionic strengths can be over-expressed in Sf9 cells or in *E. coli*.

F. Activity of Bacterially-Expressed BMRF1(1-303) in DNA Polymerase Assays

The activity of the bacterially-expressed purified BMRF1 (1-303)("ΔC303") polypeptide was examined in a DNA polymerase assay which measured incorporation of [$^{32}$P]-α-dCMP into trichloroacetic acid-precipitable material using activated calf thymus DNA and [$^{32}$P]-α-dCTP as the substrates in the presence of 100 mM ammonium sulfate (Tsurumi, T., T. Daikoku, and Y. Nishiyama, *J Virol*, 1994, 68(5): p. 3354-63). The BALF5 catalytic DNA polymerase subunit was obtained by expression in insect cells from the Ac-BALF5 baculovirus and purified by phosphocellulose and heparin affinity chromatography. The polypeptides were assayed in equimolar ratios and the specific activity (micromoles of dCMP incorporation per milligram of protein per hour) is shown in Table 3.

TABLE 3

| BALF5 | BMRF1 (1-303) | Specific Activity |
|---|---|---|
| − | − | 0.0 |
| + | − | 1.7 |
| − | + | 0.2 |
| + | + | 112.3 |

The GST-BMRF1 (1-303) polypeptide was bound to glutathione-agarose as described previously and cleaved overnight with 1/50 (w/w) factor Xa (NEBioLabs, Ipswich, Mass.) in 1 mM CaCl$_2$. The cleaved BMRF1 (1-303) was then purified on DNA-cellulose, eluting at 300-500 mM NaCl. SDS-PAGE analysis confirmed the size of the uncleaved GST-BMRF1 (1-303) and the purified cleaved BMRF1 (1-303). The purified BMRF1 (1-303) was then shown to stimulate purified baculovirus-expressed BALF5 in 100 mM ammonium sulfate (see Table 3). Thus the cleaved bacterially-expressed BMRF1 (1-303) possesses all of the functional activities known for baculovirus- and reticulocyte-expressed BMRF1-dsDNA binding and BALF5 stimulation activity.

G. Affinity Tag

The baculovirus or the *E. coli* vector comprising the BMRF1 gene, or a mutant thereof, is engineered so that the gene is fused with an affinity tag, such as 6x-his (SEQ ID NO. 7) or MBP.

Example 5. Strand-Displacement Activity ("SDA") of EBV DNA Polymerase

The EBV DNA polymerase, purified from infected cells or reconstituted from purified recombinant BALF5 and BMRF1, possesses signification SDA (Tsurumi, T., et al., *Biochem Biophys Res Commun*, 1997, 238(1): p. 33-8). Acting on a singly-primed M13mp18 single-stranded DNA circle, the EBV DNA polymerase holoenzyme synthesizes DNA chains greater than the unit length M13mp18 circle, indicating that the primer at the 5' terminus of the nascent strand has been displaced from the template. The rate of incorporation is approximately 7200 nucleotides in 10 minutes, and the SDA is not complete, since most of the reaction product is unit-length. The entire great-than-unit-length product of the reaction is sensitive to mung bean nuclease, indicating that it is single-stranded, and not the result of "snap-back" self-priming on a dissociated linear single-stranded DNA molecule. Activity comparable to the SDA of EBV DNA polymerase is not found in its homolog the HSV DNA polymerase.

A. Assays of SDA

SDA can be assayed on single-stranded DNA templates complexed with primer. As the primer is extended by the DNA polymerase, the elongation of the circular template is completed when a complete double-stranded circle is formed. For enzymes with SDA, elongation continues with displacement of the upstream strand that began with the primer. When the starting materials and products of the reaction are analyzed by agarose gel electrophoresis, the single-stranded template will migrate faster that the double-stranded product and can be easily distinguished by electrophoretic mobility. The mobility of the double-stranded product can be confirmed by comparison with authentic double-stranded DNA, which is easily obtained if an M13 ssDNA circle is used as template. SDA is defined as the activity of an enzyme which synthesizes DNAs of greater than unit length, because, in order to do so, there is displacement of the primer containing strand in order to continue copying the template. The product of strand-displacement DNA synthesis is usually heterogeneous and may be very high molecular weight DNA, since the reaction will proceed until some other factor becomes limiting. Such limiting factors would include dNTP substrates, which may be consumed in the reaction and become rate-limiting, or the intrinsic processivity of the DNA polymerase, which is a measure of how long a DNA polymerase will elongate before dissociating from the primer-template junction. Also, accumulation of bands corresponding to pausing sites due to sequence preference or secondary structure may be observed in the product. Therefore, agarose gel electrophoretic analysis of DNA synthesized by SDA reveals a heterodisperse high molecular weight DNA population that may contain many multiples of the unit-length product with relative accumulation of certain intermediates that will vary by template and the conditions of the assay.

B. Preparation of Substrates for SDA Assays on M13 Templates

Because of convenience of preparation, the filamentous bacteriophage M13 genomic DNA is used. In the M13 system, which was the foundation of the Sanger DNA sequencing method of the 1980's and 1990's, the singe-stranded DNA phage genome is found at high concentration in the medium of phage-infected *E. coli*, whereas the double-stranded phage genome replicative form is found in the infected cells themselves. Therefore, it is quite simple to obtain large amounts of highly purified single- and double-stranded DNAs of identical sequence. The "classical" 20-mer M13 sequencing primer (NEBioLabs, Ipswich, Mass.) is a ubiquitous oligonucleotide commonly found and readily available, and it is quite a good primer for the synthesis of complementary DNA in a DNA polymerase assay.

C. Synthetic Single Stranded ("ss") DNA Templates

Synthetic oligonucleotides of length 50-500 and 5'-phosphorylated or more can be circularized with bridging 20-mer oligonucleotides complementary to the 10 nucleotides on each end of the oligonucleotide to be circularized. The complex is then treated with T4 DNA ligase and purified by gel electrophoresis to remove the bridge. The synthetic circular ssDNA can then be hybridized with oligonucleotides to create substrates for gap-repair and strand-displacement reactions where the products can be accurately monitored by gel electrophoresis conveniently (Falkenberg, M. et al., *Proc Natl Acad Sci USA*, 2000, 97(8): p. 3896-900, Salinas, F. and S. J. Benkovic, *Proc Natl Acad Sci USA*, 2000, 97(13): p. 7196-201, Zhu, Y., et al., *J Virol*, 2003, 77(18): p. 10147-53).

D. Conditions for SDA Assays (Tsurumi, T., et al., *Biochem Biophys Res Commun*, 1997, 238(1): p. 33-80)

Assay buffer: 20 mM HEPES-Na pH 7.4; 2 mM MgCl$_2$; 1 mM DTT; 5% glycerol; 50 mM NaCl; 100 µg BSA/ml. Temperature: 35° C. (to be carried out at 20° C. and 50° C. in parallel). Substrates: 40 µM each dTTP and dATP. 50 ng primer-hybridized M13 ssDNA. EBVpol holoenzyme (1.0 ng). Initiation: 40 µM dGTP. 4 mM [α-32P]-dCTP (5 µCi). Quench: 5 µL 200 mM EDTA (for 30 µL assay volumes) Sampling: 20% of reaction volume every 10 minutes for 40 minutes. Analysis: Ethanol precipitation to remove unincorporated radiolabel; 0.7% alkaline agarose gel electrophoresis; 7.5% TCA, vacuum dry on DE81 paper; betascope imaging.

It is not necessary to use radioactivity for DNA polymerase assays. Polymerase assays can be carried out with fluorescent-labeled nucleotides (Cy5-dCTP) and imaging of the products displayed by agarose gel electrophoresis.

Enzymes to be assayed in parallel:
1. Bst DNA polymerase, large fragment
2. Φ29 DNA polymerase
3. Bacteriophage T4 DNA polymerase
4. Taq I DNA polymerase
5. *E. coli* DNA polymerase I, Klenow fragment
6. *E. coli* DNA polymerase I, complete
7. Vent® DNA polymerase
8. Pfu-fusion DNA polymerase Example 6. Methods for Measuring Fidelity The fidelity, or accuracy, of copying DNA by DNA polymerases is a critical property in the development of isothermal DNA amplification applications. Highly inaccurate mechanisms may produce more product more rapidly, but cannot be used for sequencing applications. In economic terms, the lower the fidelity of the enzyme used for amplification, the more expensive the sequencing operation will be, for two reasons. First, DNA samples containing more copying errors must be subjected to more sequencing runs, or "reads," in order to obtain meaningful data, and sequencing runs are quite expensive. Second, the additional information associated with the increased number of "reads," requires more data informatics analysis to produce the final result, and the labor and computing time for this procedure is costly.

The overall fidelity of a family B DNA polymerase (such as EBVpol), which determines the accuracy of copying of an amplified target, normally in the range of $10^{-6}$ to $10^{-7}$, is determined by two distinct catalytic functions: the nucleotide misinsertion rate, which is normally in the range of $10^{-4}$ to $10^{-5}$, and the proofreading function carried out by the 3'-5' exonuclease, which is normally in the range of $10^{-2}$. Fidelity can be measured in vitro by amplifying a template such as an M13 vector encoding a fragment of β-galactosidase such that an opal-reversion lacZα complementation assay can be carried out when the amplification product is transformed into bacteria that are plated out on a chromogenic substrate, allowing measurement of misincorporation rates by counting blue revertant colonies against a background of white colonies. Using such assays, the fidelity of EBVpol can be accurately measured, optimized, and compared with other polymerases.

Alternatively, high-throughput parallel sequencing can be carried out on amplified products to directly measure the fidelity of copying, by comparison and statistical analysis of multiple readings of the target sequence.

Example 7. Additional Methods

A. Assays for the Purification of BALF5 and BMRF1

The BALF5 purification is followed by dual assays of DNA polymerase activity (incorporation of fluorescent-labeled M13 forward primer into high-molecular weight product on a single-stranded M13 circular template, assayed by agarose gel electrophoresis) at low-salt and at high-salt in the presence of the purified BMRF1(1-303) polypeptide. Incorporation of dCMP radioactivity into acid-precipitable activated DNA or agarose gel analysis of incorporation into an M13 template can be carried out using [α-$^{32}$P]-dCTP, as has been well-described (Kiehl, A. and D. I. Dorsky, *Virology*, 1991, 184(1): p. 330-40. Kiehl, A. and D. I. Dorsky, *J Virol*, 1995, 69(3): p. 1669-77). The purpose of assaying column fractions under two condition is to track the presence of co-purifying DNA polymerase activity not attributable to BALF5. Purified BALF5 fractions is analyzed by SDS-PAGE and assayed for polymerase activity in the presence and absence of BMRF1, sensitivity to ionic strength, and sensitivity to the inhibitors phosphonoformic acid ("PFA") and acyclovir triphosphate (ACV-TP), which are specific for EBV DNA polymerase and do not inhibit Sf9 host-cell DNA polymerases or the baculovirus vector DNA polymerase.

B. Assays for Contaminating Activities

Assays for 5' exonuclease and endonuclease activity are carried out on BALF5 preparations used for assays of strand displacement activity. The presence of either of these activities would indicate impurity of the BALF5 preparation and would significantly affect the interpretation of results of assays of strand displacement activity.

5' exonuclease activity degrades the DNA strand encountered upstream of the polymerase carrying out chain elongation, allowing greater than unit length product on a circular template to be synthesized. However, this synthesis is not the result of strand displacement, but, rather, degradation of the upstream strand, and not properly termed "strand displacement" activity.

Endonuclease activity degrades both template and product, leading to apparent augmentation of polymerase activity due to increased initiation sites at low endonuclease activity. Whereas, at high endonuclease activity, both template and product are substantially degraded, leading to observation of diminished elongation product, independent of dNTP substrate addition.

Contaminating DNA helicase activity allows strand displacement for DNA synthesis to be carried out by a DNA polymerase lacking SDA. The assay for DNA helicase uses M13 ssDNA circles hybridized with $^{32}$P-labelled oligonucleotide (20-mer) as substrate in the presence of 1 mM ATP or dATP, assaying for displacement of labeled oligonucleotide (Crute, J. J., E. S. Mocarski, and I. R. Lehman, *Nucleic Acids Res*, 1988, 16(14A): p. 6585-96).

Salt-tolerance is an important property of the EBV DNA polymerase holoenzyme (BALF5 combined with BMRF1) and can be used to distinguish between EBV DNApol activity and other contaminating DNA polymerases which are strongly inhibited at the 100 mM $(NH_4)_2SO_4$ used in assays for EBV DNApol activity. Fractions containing BALF5 and BMRF1 to be used in assays of critical properties are assayed at low-salt to estimate the relative amount of contaminating activity. Care must be taken, however, in the assessment, since the BALF5 catalytic subunit possesses significant distributive DNA polymerase activity at low-salt in the absence of BMRF1 (Tsurumi, T., et al., *J Virol*, 1993, 67(8): p. 4651-8). However, there is virtually no processive activity of the BALF5 subunit at low-salt in the absence of BMRF1. Therefore, assays for contaminating processive strand-displacing activity at low salt using singly-primed M13 ssDNA circles should not be confounded by the presence of BALF5 that is not complexed with BMRF1 in the sample.

Some Sequences

The nucleotide sequences and amino acid sequences disclosed in the Sequence Listing as SEQ ID NOS. 1-3 and 7-8 are shown in Table 4.

TABLE 4

```
BALF5 ORF DNA sequence SEQ ID NO. 2
ATGGCTAGCGCGAGCTTAACCATGTCTGGGGGACTCTTCTATAACCCTTTCCTAAGACCTAATA
AAGGCCTTCTGAAAAAGCCTGACAAGGAGTACCTGCGTCTCATTCCCAAGTGTTTCCAGACACC
AGGCGCCGCAGGGGTGGTGGATGTGCGGGGGCCTCAGCCCCCCCTGTGCTTCTACCAAGACTCC
CTGACGGTGGTGGGGGGTGACGAGGATGGAAAGGGCATGTGGTGGCGCCAGCGTGCCCAAGAGG
GCACGGCAAGGCCGGAGGCAGACACCCACGGAAGCCCTCTGGACTTCCATGTCTACGACATACT
CGAGACGGTGTACACGCACGAGAAATGCGCCGTCATTCCATCGGATAAACAGGGGTATGTGGTG
CCATGTGGCATCGTCATCAAGCTACTGGGCCGGCGCAAGGCCGATGGGGCCAGCGTGTGTGTGA
ACGTGTTTGGGCAGCAGGCCTACTTCTACGCCAGCGCGCCTCAGGGTCTGGACGTGGAGTTTGC
AGTCCTCAGCGCCCTCAAGGCCAGCACCTTCGACCGCAGGACCCCCTGCCGGGTCTCGGTGGAG
AAGGTCACGCGCCGTTCCATTATGGGCTACGGCAACCATGCCGGCGACTACCACAAGATCACCC
TCTCCCATCCCAACAGTGTGTGTCACGTGGCCACGTGGCTGCAAGACAAGCACGGGTGTCGGAT
CTTTGAGGCCAACGTGGATGCCACGCGCCGCTTTGTCCTGGACAATGACTTTGTCACCTTTGGC
TGGTACAGCTGCCGCCGCGCCATCCCCCGCCTCCAGCACCGGGACTCGTACGCCGAGCTCGAGT
ACGACTGTGAGGTGGGCGACCTCTCGGTCCGGCGTGAAGACAGCTCCTGGCCCTCCTACCAGGC
CCTGGCCTTCGATATCGAGTGTCTGGGGGAGGAGGGCTTCCCCACGGCCACCAACGAGGCTGAC
CTGATCCTGCAGATATCCTGCGTCCTCTGGTCGACAGGGGAGGAGGCCGGGCGCTATAGGCGCA
TCCTGCTGACGCTGGGCACCTGCGAAGACATAGAGGGGGTTGAGGTCTACGAGTTCCCATCGGA
GCTGGACATGCTCTACGCCTTCTTCCAGCTCATCAGAGACCTCAGCGTGGAGATTGTGACCGGC
TACAACGTGGCCAACTTTGACTGGCCCTACATTCTGGACAGAGCCAGGCACATCTACAGCATCA
ACCCAGCCTCTCTGGGCAAAATTAGGGCTGGGGGCGTCTGCGAGGTCAGGCGACCCCATGATGC
GGGCAAGGGCTTCTTGCGGGCCAACACCAAGGTCCGCATCACCGGCCTCATCCCCATCGACATG
TACGCCGTGTGCCGGGACAAGCTCAGCCTCTCAGACTACAAGCTGGACACAGTAGCCAGGCACC
TACTGGGGGCCAAGAAGGAGGATGTGCATTACAAGGAGATTCCTCGCCTCTTTGCAGCGGGCCC
CGAGGGGCGCAGGCGGCTCGGCATGTACTGCGTGCAGGACTCGGCCCTGGTCATGGATCTGCTA
AACCATTTCGTGATCCACGTGGAGGTGGCAGAGATTGCCAAGATCGCTCACATCCCCTGCAGGC
GGGTGCTGGACGATGGGCAGCAGATCCGCGTGTTCTCCTGCCTCCTGGCGGCCGCCCAAAAGGA
AAACTTTATCCTGCCCATGCCCTCGGCCTCTGACCGGGACGGCTACCAGGGGGCCACCGTCATC
CAGCCCCTGTCCGGATTCTACAACTCCCCGGTTCTGGTGGTGGACTTTGCCAGCCTCTACCCGA
GCATCATTCAGGCTCATAATCTCTGTTATTCTACCATGATAACGCCGGGAGAAGAGCACAGGCT
AGCCGGCCTGCGCCCGGGAGAAGACTATGAGTCCTTCAGGCTCACGGGGGGCGTCTACCACTTT
GTAAAGAAGCACGTGCACGAGTCCTTCTTGGCTAGTCTGTTGACCTCCTGGCTGGCCAAGCGCA
AGGCCATCAAGAAGCTGCTGGCGGCCTGCGAGGATCCGCGCCAAAGGACCATCCTCGACAAGCA
GCAGCTGGCCATCAAGTGCACGTGCAACGCCGTCTACGGCTTCACCGGGGTGGCCAACGGCCTC
TTTCCCTGCCTCTCCATCGCCGAGACGGTGACGCTGCAGGGCCGCACGATGTTGGAGCGGGCCA
AGGCCTTCGTGGAGGCCCTGAGCCCCGCCAACCTGCAGGCCCTGGCCCCCTCCCCGGACGCCTG
```

TABLE 4-continued

```
GGCGCCCCTCAACCCCGAGGGCCAGCTTCGAGTCATCTACGGGGACACGGACTCGCTGTTTATC
GAGTGCCGGGGGTTTTCAGAGAGCGAGACCCTGCGCTTTGCCGATGCCCTGGCCGCCCACACCA
CCCGGAGCCTGTTTGTGGCCCCCATCTCCCTGGAGGCCGAGAAGACCTTCTCCTGCCTGATGCT
GATTACAAAGAAGAGATATGTGGGGGTGCTGACGGACGGCAAGACCCTGATGAAGGGGGTGGAG
CTCGTCCGGAAGACGGCCTGCAAGTTTGTGCAGACACGCTGCCGGCGCGTGCTCGACCTGGTGC
TGGCGGATGCCCGGGTAAAGGAGGCGGCCAGCCTCCTCTCCCACCGGCCCTTCCAAGAGTCATT
TACACAAGGGCTACCTGTGGGCTTTTTGCCCGTCATTGACATCCTAAACCAGGCCTACACAGAC
CTCCGTGAAGGCAGGGTCCCCATGGGGGAGCTCTGCTTTTCAACGGAGCTCAGCCGCAAGCTCT
CAGCCTACAAGAGCACCCAGATGCCTCACCTGGCCGTCTACCAGAAGTTCGTCGAGCGCAACGA
GGAACTGCCCCAGATCCACGACCGCATCCAGTACGTCTTTGTGGAGCCCAAGGGGGGAGTGAAG
GGGGCGAGAAAGACGGAGATGGCCGAGGACCCGGCCTACGCCGAGCGGCACGGCGTTCCCGTGG
CCGTGGATCATTATTTCGACAAGCTGCTCCAAGGAGCGGCCAACATCCTCCAGTGCCTCTTTGA
TAACAACTCCGGGGCCGCCCTCTCCGTCCTCCAGAATTTTACAGCCCGGCCACCATTCTAA

BMRF1 ORF DNA sequence SEQ ID NO. 1
ATGGAAACCACTCAGACTCTCCGCTTTAAGACCAAGGCCCTAGCCGTCCTGTCCAAGTGCTATG
ACCATGCCCAGACTCATCTCAAGGGAGGAGTGCTGCAGGTAAACCTTCTGTCTGTAAACTATGG
AGGCCCCCGGCTGGCCGCCGTGGCCAACGCAGGCACGGCCGGGCTAATCAGCTTCGAGGTCTCC
CCTGACGCTGTGGCCGAGTGGCAGAATCACCAGAGCCCAGAGGAGGCCCCGGCCGCCGTGTCAT
TTAGAAACCTTGCCTACGGGCGCACCTGTGTCCTGGGCAAGGAGCTGTTTGGCTCGGCTGTGGA
GCAGGCTTCCCTGCAATTTTACAAGCGGCCACAAGGGGGTTCCCGGCCTGAATTTGTTAAGCTC
ACTATGGAATATGATGATAAGGTGTCCAAGAGCCACCACACCTGCGCCCTGATGCCCTATATGC
CCCCGGCCAGCGACAGGCTGAGGAACGAGCAGATGATTGGGCAGGTGCTGTTGATGCCCAAGAC
GGCTTCCTCGTTGCAGAAGTGGGCACGCCAGCAAGGCTCAGGCGGCGTTAAGGTGACACTCAAT
CCGGATCTCTACGTCACCACGTATACTTCTGGGGAGGCCTGCCTCACCCTAGACTACAAGCCTC
TGAGTGTGGGGCCATACGAGGCCTTCACTGGCCCTGTGCCAAGGCTCAGGACGTGGGGGCCGT
TGAGGCCCACGTTGTCTGCTCGGTAGCAGCGGACTCGCTGGCGGCGGCGCTTAGCCTCTGCCGC
ATTCCGGCCGTTAGCGTGCCAATCTTGAGGTTTTACAGGTCTGGCATCATAGCTGTGGTGGCCG
GCCTGCTGACGTCAGCGGGGGACCTGCCGTTGGATCTTAGTGTTATTTTATTTAACCACGCCTC
CGAAGAGGCGGCCGCCAGTACGGCCTCTGAGCCAGAAGATAAAGTCCCCGGGTGCAACCACTG
GGCACAGGACTCCAACAACGCCCCAGACATACGGTCAGTCCATCTCCTTCACCTCCGCCACCTC
CTAGGACCCCTACTTGGGAGAGTCCGGCAAGGCCAGAGACACCCTCGCCTGCCATTCCCAGCCA
CTCCAGCAACACCGCACTGGAGAGGCCTCTGGCTGTTCAGCTCGCGAGGAAAAGGACATCGTCG
GAGGCCAGGCAGAAGCAGAAGCACCCCAAGAAAGTGAAGCAGGCCTTTAACCCCCTCATTTAA GST-BMRF1(1-303) ORF DNA sequence SEQ ID NO. 3
ATGTCCCCTATACTAGGTTATTGGAAAATTAAGGGCCTTGTGCAACCCACTCGACTTCTTTTGG
AATATCTTGAAGAAAAATATGAAGAGCATTTGTATGAGCGCGATGAAGGTGATAAATGGCGAAA
CAAAAAGTTTGAATTGGGTTTGGAGTTTCCCAATCTTCCTTATTATATTGATGGTGATGTTAAA
TTAACACAGTCTATGGCCATCATACGTTATATAGCTGACAAGCACAACATGTTGGGTGGTTGTC
CAAAAGAGCGTGCAGAGATTTCAATGCTTGAAGGAGCGGTTTTGGATATTAGATACGGTGTTTC
GAGAATTGCATATAGTAAAGACTTTGAAACTCTCAAAGTTGATTTTCTTAGCAAGCTACCTGAA
ATGCTGAAAATGTTCGAAGATCGTTTATGTCATAAAACATATTTAAATGGTGATCATGTAACCC
ATCCTGACTTCATGTTGTATGACGCTCTTGATGTTGTTTTATACATGGACCCAATGTGCCTGGA
TGCGTTCCCAAAATTAGTTTGTTTTAAAAAACGTATTGAAGCTATCCACAAATTGATAAGTAC
TTGAAATCCAGCAAGTATATAGCATGGCCTTTGCAGGGCTGGCAAGCACGTTTGGTGGTGGCG
ACCATCCTCCAAATCGGATCTGGTTCCGCGTGGATCAGCTTGGTACCGAGCTCGGATCATGGA
AACCACTCAGACTCTCCGCTTTAAGACCAAGGCCCTAGCCGTCCTGTCCAAGTGCTATGACCAT
GCCCAGACTCATCTCAAGGGAGGAGTGCTGCAGGTAAACCTTCTGTCTGTAAACTATGGAGGCC
CCCGGCTGGCCGCCGTGGCCAACGCAGGCACGGCCGGGCTAATCAGCTTCGAGGTCTCCCCTGA
CGCTGTGGCCGAGTGGCAGAATCACCAGAGCCCAGAGGAGGCCCCGGCCGCCGTGTCATTTAGA
AACCTTGCCTACGGGCGCACCTGTGTCCTGGGCAAGGAGCTGTTTGGCTCGGCTGTGGAGCAGG
CTTCCCTGCAATTTTACAAGCGGCCACAAGGGGGTTCCCGGCCTGAATTTGTTAAGCTCACTAT
GGAATATGATGATAAGGTGTCCAAGAGCCACCACACCTGCGCCCTGATGCCCTATATGCCCCCG
GCCAGCGACAGGCTGAGGAACGAGCAGATGATTGGGCAGGTGCTGTTGATGCCCAAGACGGCTT
CCTCGTTGCAGAAGTGGGCACGCCAGCAAGGCTCAGGCGGCGTTAAGGTGACACTCAATCCGGA
TCTCTACGTCACCACGTATACTTCTGGGGAGGCCTGCCTCACCCTAGACTACAAGCCTCTGAGT
GTGGGGCCATACGAGGCCTTCACTGGCCCTGTGCCAAGGCTCAGGACGTGGGGGCCGTTGAGG
CCCACGTTGTCTGCTCGGTAGCAGCGGACTCGCTGGCGGCGGCGCTTAGCCTCTGCCGCATTCC
GGCCGTTAGCGTGCCAATCTTGAGGTTTTACAGGTCTGGCATCATAGCTGTGGTGGCCGGCCTG
CTGACGTCAGCGGGGGACCTGCCGTTGGATCTTAGTGTTATTTTATTTAACCACGCCTCCGAAG
AGGCGGCCCTAGAATTCATCGTGACTGACTGA BALF5 protein sequence SEQ ID NO. 8
MASASLTMSGGLFYNPFLRPNKGLLKKPDKEYLRLIPKCFQTPGAAGVVDVRGPQPPLCFYQDS
LTVVGGDEDGKGMWWRQRAQEGTARPEADTHGSPLDPHVYDILETVYTHEKCAVIPSDKQGYVV
PCGIVIKLLGRRKADGASVCVNVFGQQAYFYASAPQGLDVEFAVLSALKASTFDRRTPCRVSVE
KVTRRSIMGYGNHAGDYHKITLSHPNSVCHVATWLQDKHGCRIFEANVDATRRFVLDNDFVTFG
WYSCRRAIPRLQHRDSYAELEYDCEVGDLSVRREDSSWPSYQALAFDIECLGEEGFPTATNEAD
LILQISCVLWSTGEEAGRYRRILLTLGTCEDIEGVEVYEFPSELDMLYAFFQLIRDLSVEIVTG
YNVANFDWPYILDRARHIYSINPASLGKIRAGGVCEVRRPHDAGKGFLRANTKVRITGLIPIDM
YAVCRDKLSLSDYKLDTVARHLLGAKKEDVHYKEIPRLFAAGPEGRRRLGMYCVQDSALVMDLL
NHFVIHVEVAEIAKIAHIPCRRVLDDGQQIRVFSCLLAAAQKENFILPMPSASDRDGYQGATVI
QPLSGFYNSPVLVVDFASLYPSIIQAHNLCYSTMITPGEEHRLAGLRPGEDYESFRLTGGVYHF
VKKHVHESFLASLLTSWLAKRKAIKKLLAACEDPRQRTILDKQQLAIKCTCNAVYGFTGVANGL
FPCLSIAETVTLQGRTMLERAKAFVEALSPANLQALAPSPDAWAPLNPEGQLRVIYGDTDSLFI
ECRGFSESETLRFADALAAHTTRSLFVAPISLEAEKTFSCLMLITKKRYVGVLTDGKTLMKGVE
```

TABLE 4-continued

```
LVRKTACKFVQTRCRRVLDLVLADARVKEAASLLSHRPFQESFTQGLPVGFLPVIDILNQAYTD
LREGRVPMGELCFSTELSRKLSAYKSTQMPHLAVYQKFVERNEELPQIHDRIQYVFVEPKGGVK
GARKTEMAEDPAYAERHGVPVAVDHYFDKLLQGAANILQCLFDNNSGAALSVLQNFTARPPF

BMRF1 protein sequence SEQ ID NO. 9
METTQTLRFKTKALAVLSKCYDHAQTHLKGGVLQVNLLSVNYGGPRLAAVANAGTAGLISFEVS
PDAVAEWQNHQSPEEAPAAVSFRNLAYGRTCVLGKELFGSAVEQASLQFYKRPQGGSRPEFVKL
TMEYDDKVSKSHHTCALMPYMPPASDRLRNEQMIGQVLLMPKTASSLQKWARQQGSGGVKVTLN
PDLYVTTYTSGEACLTLDYKPLSVGPYEAFTGPVAKAQDVGAVEAHVVCSVAADSLAAALSLCR
IPAVSVPILRFYRSGIIAVVAGLLTSAGDLPLDLSVILFNHASEEAAASTASEPEDKSPRVQPL
GTGLQQRPRHTVSPSPSPPPPPRTPTWESPARPETPSPAIPSHSSNTALERPLAVQLARKRTSS
EARQKQKHPKKVKQAFNPLI
```

All patents, patent publications, and references mentioned herein are incorporated by reference.

The foregoing description discloses only exemplary embodiments of the invention. Modifications of the above disclosed modified EBV polymerases, methods, and kits which fall within the scope of the invention will be readily apparent to those of ordinary skill in the art.

While only certain features of the invention have been illustrated and described, many modifications and changes will occur to those skilled in the art. It is therefore to be understood that the appended claims are intended to cover all such modifications and changes as fall within the true spirit of the invention.

I claim:

1. A method for amplifying a target nucleic acid sample sequence in vitro, the method comprising:
    (a) mixing a set of primers with a target nucleic acid sample sequence and incubating the primer-target sample mixture under conditions that promote and/or optimize amplification of the target nucleic acid sequence in step (c) below;
    (b) adding an EBV DNA polymerase comprising a BALF5 subunit polypeptide that is a wild type BALF5 subunit, with a 6-histidine residue carboxyl terminal tag and/or an amino terminal GST tag, and a BMRF1 subunit with a carboxyl-terminal deletion of residues 304-404, to the primer-target sample mixture of (a), to produce a polymerase-primer-target sample mixture and incubating the polymerase-primer-target sample mixture under conditions that promote and/or optimize replication of the target sequence, wherein replication of the target sequence results in replicated strands, wherein during replication at least one of the replicated strands is displaced from the target sequence by strand displacement replication of another replicated strand and
    (c) amplifying the target nucleic acid; wherein the amplification results in about 2 ug to about 10 ug of DNA; wherein neither step (a) nor step (b) involves thermal cycling.

* * * * *

SEQUENCE LISTING

```
<160> NUMBER OF SEQ ID NOS: 9

<210> SEQ ID NO 1
<211> LENGTH: 1215
<212> TYPE: DNA
<213> ORGANISM: Epstein-Barr virus

<400> SEQUENCE: 1
atggaaacca ctcagactct ccgctttaag accaaggccc tagccgtcct gtccaagtgc      60
tatgaccatg cccagactca tctcaaggga ggagtgctgc aggtaaacct tctgtctgta     120 aactatgag gcccccggct ggccgccgtg gccaacgcag gcacggccgg gctaatcagc     180
ttcgaggtct cccctgacgc tgtggccgag tgcagaatc accagagccc agaggaggcc     240
ccggccgccg tgtcatttag aaaccttgcc tacgggcgca cctgtgtcct gggcaaggag     300
ctgtttggct cggctgtgga gcaggcttcc ctgcaatttt acaagcggcc acaaggggt     360 tcccggcctg aatttgttaa gctcactatg gaatatgatg ataaggtgtc caagagccac     420
cacacctgcg ccctgatgcc ctatatgccc ccggccagcg acaggctgag gaacgagcag     480 atgattggc aggtgctgtt gatgcccaag acggcttcct cgttgcagaa gtgggcacgc     540
cagcaaggct caggcggcgt taaggtgaca ctcaatccgg atctctacgt caccacgtat     600
acttctgggg aggcctgcct caccctagac tacaagcctc tgagtgtggg gccatacgag     660
gccttcactg gccctgtggc caaggctcag gacgtggggg ccgttgaggc ccacgttgtc     720
tgctcggtag cagcggactc gctggcggcg gcgcttagcc tctgccgcat tccggccgtt     780
agcgtgccaa tcttgaggtt ttacaggtct ggcatcatag ctgtggtggc cggcctgctg     840
acgtcagcgg ggacctgcc gttggatctt agtgttattt tatttaacca cgcctccgaa     900
gaggcggccg ccagtacggc ctctgagcca gaagataaaa gtccccgggt gcaaccactg     960
ggcacaggac tccaacaacg ccccagacat acggtcagtc catctccttc acctccgcca    1020
cctcctagga cccctacttg ggagagtccg gcaaggccag agacaccctc gcctgccatt    1080
cccagccact ccagcaacac cgcactggag aggcctctgg ctgttcagct cgcgaggaaa    1140
aggacatcgt cggaggccag gcagaagcag aagcacccca agaaagtgaa gcaggccttt    1200
aaccccctca tttaa                                                     1215
```

<210> SEQ ID NO 2
<211> LENGTH: 3069
<212> TYPE: DNA
<213> ORGANISM: Epstein-Barr virus

<400> SEQUENCE: 2

| | | | | | |
|---|---|---|---|---|---|
| atggctagcg | cgagcttaac | catgtctggg | ggactcttct | ataacccttt | cctaagacct | 60 |
| aataaaggcc | ttctgaaaaa | gcctgacaag | gagtacctgc | gtctcattcc | caagtgtttc | 120 |
| cagacaccag | gcgccgcagg | ggtggtggat | gtgcggggc | ctcagccccc | cctgtgcttc | 180 |
| taccaagact | ccctgacggt | ggtgggggt | gacgaggatg | gaagggcat | gtggtggcgc | 240 |
| cagcgtgccc | aagagggcac | ggcaaggccg | gaggcagaca | cccacggaag | ccctctggac | 300 |
| ttccatgtct | acgacatact | cgagacggtg | tacgcgcacg | agaaatgcgc | cgtcattcca | 360 |
| tcggataaac | agggg tatgt | ggtgccatgt | ggcatcgtca | tcaagctact | gggccggcgc | 420 |
| aaggccgatg | gggccagcgt | gtgtgtgaac | gtgtttgggc | agcaggccta | cttctacgcc | 480 |
| agcgcgcctc | agggtctgga | cgtggagttt | gcagtcctca | gcgccctcaa | ggccagcacc | 540 |
| ttcgaccgca | ggacccctg | ccgggtctcg | gtggagaagg | tcacgcgccg | ttccattatg | 600 |
| ggctacggca | ccatgccgg | cgactaccac | aagatcaccc | tctcccatcc | caacagtgtg | 660 |
| tgtcacgtgg | ccacgtggct | gcaagacaag | cacgggtgtc | ggatctttga | ggccaacgtg | 720 |
| gatgccacgc | gccgctttgt | cctggacaat | gactttgtca | cctttggctg | gtacagctgc | 780 |
| cgccgcgcca | tccccgcct | ccagcaccgg | gactcgtacg | ccgagctcga | gtacgactgt | 840 |
| gaggtgggcg | acctctcggt | ccggcgtgaa | gacagctcct | ggccctccta | ccaggccctg | 900 |
| gccttcgata | tcgagtgtct | ggggaggag | ggcttcccca | cggccaccaa | cgaggctgac | 960 |
| ctgatcctgc | agatatcctg | cgtcctctgg | tcgacagggg | aggaggccgg | gcgctatagg | 1020 |
| cgcatcctgc | tgacgctggg | cacctgcgaa | gacatagagg | gggttgaggt | ctacgagttc | 1080 |
| ccatcggagc | tggacatgct | ctacgccttc | ttccagctca | tcagagacct | cagcgtggag | 1140 |
| attgtgaccg | gctacaacgt | ggccaacttt | gactggccct | acattctgga | cagagccagg | 1200 |
| cacatctaca | gcatcaaccc | agcctctctg | ggcaaaatta | gggctgggg | cgtctgcgag | 1260 |
| gtcaggcgac | cccatgatgc | gggcaagggc | ttcttgcggg | ccaacaccaa | ggtccgcatc | 1320 |
| accggcctca | tccccatcga | catgtacgcc | gtgtgccggg | acaagctcag | cctctcagac | 1380 |
| tacaagctgg | acacagtagc | caggcaccta | ctgggggcca | agaaggagga | tgtgcattac | 1440 |
| aaggagattc | ctcgcctctt | tgcagcgggc | cccgagggc | gcaggcggct | cggcatgtac | 1500 |
| tgcgtgcagg | actcggccct | ggtcatggat | ctgctaaacc | atttcgtgat | ccacgtggag | 1560 |
| gtggcagaga | ttgccaagat | cgctcacatc | ccctgcaggc | gggtgctgga | cgatgggcag | 1620 |
| cagatccgcg | tgttctcctg | cctcctggcg | ccgcccaaa | aggaaaactt | tatcctgccc | 1680 |
| atgccctcgg | cctctgaccg | ggacggctac | caggggggcca | ccgtcatcca | gcccctgtcc | 1740 |
| ggattctaca | actccccggt | tctggtggtg | gacttttgcca | gcctctaccc | gagcatcatt | 1800 |
| caggctcata | atctctgtta | ttctaccatg | ataacgccgg | gagaagagca | caggctagcc | 1860 |
| ggcctgcgcc | cggagaagaa | ctatgagtcc | ttcaggctca | cgggggggcgt | ctaccacttt | 1920 |
| gtaaagaagc | acgtgcacga | gtccttcttg | gctagtctgt | tgacctcctg | gctggccaag | 1980 |
| cgcaaggcca | tcaagaagct | gctggcggcc | tgcgaggatc | cgcgccaaag | gaccatcctc | 2040 |
| gacaagcagc | agctgccat | caagtgcacg | tgcaacgccg | tctacggctt | caccggggtg | 2100 |
| gccaacggcc | tctttccctg | cctctccatc | gccgagacgg | tgacgctgca | gggccgcacg | 2160 |

```
atgttggagc gggccaaggc cttcgtggag gccctgagcc ccgccaacct gcaggccctg   2220
gccccctccc cggacgcctg ggcgcccctc aaccccgagg gccagcttcg agtcatctac   2280
ggggacacgg actcgctgtt tatcgagtgc cgggggtttt cagagagcga gaccctgcgc   2340
tttgccgatg ccctggccgc ccacaccacc cggagcctgt ttgtggcccc catctccctg   2400
gaggccgaga agaccttctc ctgcctgatg ctgattacaa agaagagata tgtgggggtg   2460
ctgacggacg gcaagaccct gatgaagggg gtggagctcg tccggaagac ggcctgcaag   2520
tttgtgcaga cacgctgccg gcgcgtgctc gacctggtgc tggcggatgc ccgggtaaag   2580
gaggcggcca gcctcctctc ccaccggccc ttccaagagt catttacaca agggctacct   2640
gtgggctttt tgcccgtcat tgacatccta aaccaggcct acacagacct ccgtgaaggc   2700
agggtcccca tgggggagct ctgcttttca acggagctca gccgcaagct ctcagcctac   2760
aagagcaccc agatgcctca cctggccgtc taccagaagt tcgtcgagcg caacgaggaa   2820
ctgccccaga tccacgaccg catccagtac gtctttgtgg agcccaaggg gggagtgaag   2880
ggggcgagaa agacggagat ggccgaggac ccggcctacg ccgagcggca cggcgttccc   2940
gtggccgtgg atcattattt cgacaagctg ctccaaggag cggccaacat cctccagtgc   3000
ctctttgata acaactccgg ggccgccctc tccgtcctcc agaattttac agcccggcca   3060
ccattctaa                                                           3069
```

<210> SEQ ID NO 3
<211> LENGTH: 1632
<212> TYPE: DNA
<213> ORGANISM: Epstein-Barr virus

<400> SEQUENCE: 3

```
atgtccccta tactaggtta ttggaaaatt aagggccttg tgcaacccac tcgacttctt     60
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga aatccagcaa gtatatagca    600
tggcctttgc agggctggca agccacgttt ggtggtggcg accatcctcc aaaatcggat    660
ctggttccgc gtggatcagc ttggtaccga gctcggatca tggaaaccac tcagactctc    720
cgctttaaga ccaaggccct agccgtcctg tccaagtgct atgaccatgc ccagactcat    780
ctcaagggag gagtgctgca ggtaaacctt ctgtctgtaa actatggagg cccccggctg    840
gccgccgtgg ccaacgcagg cacggccggg ctaatcagct tcgaggtctc ccctgacgct    900
gtggccgagt ggcagaatca ccagagccca gaggaggccc cggccgccgt gtcatttaga    960
aaccttgcct acgggcgcac ctgtgtcctg ggcaaggagc tgtttggctc ggctgtggag   1020
caggcttccc tgcaatttta caagcggcca caagggggtt cccggcctga atttgttaag   1080
ctcactatgg aatatgatga taaggtgtcc aagagccacc acacctgcgc cctgatgccc   1140
```

-continued

```
tatatgcccc cggccagcga caggctgagg aacgagcaga tgattgggca ggtgctgttg    1200
atgcccaaga cggcttcctc gttgcagaag tgggcacgcc agcaaggctc aggcggcgtt    1260
aaggtgacac tcaatccgga tctctacgtc accacgtata cttctgggga ggcctgcctc    1320
accctagact acaagcctct gagtgtgggg ccatacgagg ccttcactgg ccctgtggcc    1380
aaggctcagg acgtggggc cgttgaggcc cacgttgtct gctcggtagc agcggactcg    1440
ctggcggcgg cgcttagcct ctgccgcatt ccggccgtta gcgtgccaat cttgaggttt    1500
tacaggtctg gcatcatagc tgtggtggcc ggcctgctga cgtcagcggg ggacctgccg    1560
ttggatctta gtgttatttt atttaaccac gcctccgaag aggcggccct agaattcatc    1620
gtgactgact ga                                                        1632
```

<210> SEQ ID NO 4
<211> LENGTH: 5
<212> TYPE: PRT
<213> ORGANISM: Epstein-Barr virus

<400> SEQUENCE: 4

Gly Asp Thr Asp Ser
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Asp Thr Asp Ala
1               5

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccggaattcc gg                                                           12

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 7

His His His His His His
1               5

<210> SEQ ID NO 8
<211> LENGTH: 1022
<212> TYPE: PRT
<213> ORGANISM: Epstein-Barr Virus

<400> SEQUENCE: 8

Met Ala Ser Ala Ser Leu Thr Met Ser Gly Gly Leu Phe Tyr Asn Pro

-continued

```
1               5                    10                   15
Phe Leu Arg Pro Asn Lys Gly Leu Leu Lys Pro Asp Lys Glu Tyr
             20                  25                  30
Leu Arg Leu Ile Pro Lys Cys Phe Gln Thr Pro Gly Ala Ala Val
             35                  40                  45
Val Asp Val Arg Gly Pro Gln Pro Pro Leu Cys Phe Tyr Gln Asp Ser
 50                  55                  60
Leu Thr Val Val Gly Gly Asp Glu Asp Gly Lys Gly Met Trp Trp Arg
 65                  70                  75                  80
Gln Arg Ala Gln Glu Gly Thr Ala Arg Pro Glu Ala Asp Thr His Gly
                     85                  90                  95
Ser Pro Leu Asp Phe His Val Tyr Asp Ile Leu Glu Thr Val Tyr Thr
             100                 105                 110
His Glu Lys Cys Ala Val Ile Pro Ser Asp Lys Gln Gly Tyr Val Val
             115                 120                 125
Pro Cys Gly Ile Val Ile Lys Leu Leu Gly Arg Arg Lys Ala Asp Gly
 130                 135                 140
Ala Ser Val Cys Val Asn Val Phe Gly Gln Gln Ala Tyr Phe Tyr Ala
 145                 150                 155                 160
Ser Ala Pro Gln Gly Leu Asp Val Glu Phe Ala Val Leu Ser Ala Leu
                 165                 170                 175
Lys Ala Ser Thr Phe Asp Arg Arg Thr Pro Cys Arg Val Ser Val Glu
             180                 185                 190
Lys Val Thr Arg Arg Ser Ile Met Gly Tyr Gly Asn His Ala Gly Asp
             195                 200                 205
Tyr His Lys Ile Thr Leu Ser His Pro Asn Ser Val Cys His Val Ala
 210                 215                 220
Thr Trp Leu Gln Asp Lys His Gly Cys Arg Ile Phe Glu Ala Asn Val
 225                 230                 235                 240
Asp Ala Thr Arg Arg Phe Val Leu Asp Asn Asp Phe Val Thr Phe Gly
                 245                 250                 255
Trp Tyr Ser Cys Arg Arg Ala Ile Pro Arg Leu Gln His Arg Asp Ser
             260                 265                 270
Tyr Ala Glu Leu Glu Tyr Asp Cys Glu Val Gly Asp Leu Ser Val Arg
             275                 280                 285
Arg Glu Asp Ser Ser Trp Pro Ser Tyr Gln Ala Leu Ala Phe Asp Ile
 290                 295                 300
Glu Cys Leu Gly Glu Glu Gly Phe Pro Thr Ala Thr Asn Glu Ala Asp
 305                 310                 315                 320
Leu Ile Leu Gln Ile Ser Cys Val Leu Trp Ser Thr Gly Glu Glu Ala
                 325                 330                 335
Gly Arg Tyr Arg Arg Ile Leu Leu Thr Leu Gly Thr Cys Glu Asp Ile
             340                 345                 350
Glu Gly Val Glu Val Tyr Glu Phe Pro Ser Glu Leu Asp Met Leu Tyr
             355                 360                 365
Ala Phe Phe Gln Leu Ile Arg Asp Leu Ser Val Glu Ile Val Thr Gly
 370                 375                 380
Tyr Asn Val Ala Asn Phe Asp Trp Pro Tyr Ile Leu Asp Arg Ala Arg
 385                 390                 395                 400
His Ile Tyr Ser Ile Asn Pro Ala Ser Leu Gly Lys Ile Arg Ala Gly
                 405                 410                 415
Gly Val Cys Glu Val Arg Arg Pro His Asp Ala Gly Lys Gly Phe Leu
             420                 425                 430
```

```
Arg Ala Asn Thr Lys Val Arg Ile Thr Gly Leu Ile Pro Ile Asp Met
        435                 440                 445

Tyr Ala Val Cys Arg Asp Lys Leu Ser Leu Ser Asp Tyr Lys Leu Asp
    450                 455                 460

Thr Val Ala Arg His Leu Leu Gly Ala Lys Lys Glu Asp Val His Tyr
465                 470                 475                 480

Lys Glu Ile Pro Arg Leu Phe Ala Ala Gly Pro Glu Gly Arg Arg
                485                 490                 495

Leu Gly Met Tyr Cys Val Gln Asp Ser Ala Leu Val Met Asp Leu Leu
            500                 505                 510

Asn His Phe Val Ile His Val Glu Val Ala Glu Ile Ala Lys Ile Ala
        515                 520                 525

His Ile Pro Cys Arg Arg Val Leu Asp Asp Gly Gln Gln Ile Arg Val
        530                 535                 540

Phe Ser Cys Leu Leu Ala Ala Ala Gln Lys Glu Asn Phe Ile Leu Pro
545                 550                 555                 560

Met Pro Ser Ala Ser Asp Arg Asp Gly Tyr Gln Gly Ala Thr Val Ile
                565                 570                 575

Gln Pro Leu Ser Gly Phe Tyr Asn Ser Pro Val Leu Val Val Asp Phe
            580                 585                 590

Ala Ser Leu Tyr Pro Ser Ile Ile Gln Ala His Asn Leu Cys Tyr Ser
        595                 600                 605

Thr Met Ile Thr Pro Gly Glu Glu His Arg Leu Ala Gly Leu Arg Pro
        610                 615                 620

Gly Glu Asp Tyr Glu Ser Phe Arg Leu Thr Gly Gly Val Tyr His Phe
625                 630                 635                 640

Val Lys Lys His Val His Glu Ser Phe Leu Ala Ser Leu Leu Thr Ser
                645                 650                 655

Trp Leu Ala Lys Arg Lys Ala Ile Lys Lys Leu Leu Ala Ala Cys Glu
            660                 665                 670

Asp Pro Arg Gln Arg Thr Ile Leu Asp Lys Gln Gln Leu Ala Ile Lys
        675                 680                 685

Cys Thr Cys Asn Ala Val Tyr Gly Phe Thr Gly Val Ala Asn Gly Leu
        690                 695                 700

Phe Pro Cys Leu Ser Ile Ala Glu Thr Val Thr Leu Gln Gly Arg Thr
705                 710                 715                 720

Met Leu Glu Arg Ala Lys Ala Phe Val Glu Ala Leu Ser Pro Ala Asn
                725                 730                 735

Leu Gln Ala Leu Ala Pro Ser Pro Asp Ala Trp Ala Pro Leu Asn Pro
            740                 745                 750

Glu Gly Gln Leu Arg Val Ile Tyr Gly Asp Thr Asp Ser Leu Phe Ile
        755                 760                 765

Glu Cys Arg Gly Phe Ser Glu Ser Glu Thr Leu Arg Phe Ala Asp Ala
        770                 775                 780

Leu Ala Ala His Thr Thr Arg Ser Leu Phe Val Ala Pro Ile Ser Leu
785                 790                 795                 800

Glu Ala Glu Lys Thr Phe Ser Cys Leu Met Leu Ile Thr Lys Lys Arg
                805                 810                 815

Tyr Val Gly Val Leu Thr Asp Gly Lys Thr Leu Met Lys Gly Val Glu
            820                 825                 830

Leu Val Arg Lys Thr Ala Cys Lys Phe Val Gln Thr Arg Cys Arg Arg
        835                 840                 845
```

```
Val Leu Asp Leu Val Leu Ala Asp Ala Arg Val Lys Glu Ala Ala Ser
    850                 855                 860

Leu Leu Ser His Arg Pro Phe Gln Glu Ser Phe Thr Gln Gly Leu Pro
865                 870                 875                 880

Val Gly Phe Leu Pro Val Ile Asp Ile Leu Asn Gln Ala Tyr Thr Asp
                885                 890                 895

Leu Arg Glu Gly Arg Val Pro Met Gly Glu Leu Cys Phe Ser Thr Glu
                900                 905                 910

Leu Ser Arg Lys Leu Ser Ala Tyr Lys Ser Thr Gln Met Pro His Leu
                915                 920                 925

Ala Val Tyr Gln Lys Phe Val Glu Arg Asn Glu Leu Pro Gln Ile
    930                 935                 940

His Asp Arg Ile Gln Tyr Val Phe Val Glu Pro Lys Gly Gly Val Lys
945                 950                 955                 960

Gly Ala Arg Lys Thr Glu Met Ala Glu Asp Pro Ala Tyr Ala Glu Arg
                965                 970                 975

His Gly Val Pro Val Ala Val Asp His Tyr Phe Asp Lys Leu Leu Gln
                980                 985                 990

Gly Ala Ala Asn Ile Leu Gln Cys  Leu Phe Asp Asn Asn  Ser Gly Ala
                995                1000                1005

Ala Leu  Ser Val Leu Gln Asn  Phe Thr Ala Arg Pro  Pro Phe
    1010                1015                1020

<210> SEQ ID NO 9
<211> LENGTH: 404
<212> TYPE: PRT
<213> ORGANISM: Epstein-Barr Virus

<400> SEQUENCE: 9

Met Glu Thr Thr Gln Thr Leu Arg Phe Lys Thr Lys Ala Leu Ala Val
1               5                   10                  15

Leu Ser Lys Cys Tyr Asp His Ala Gln Thr His Leu Lys Gly Gly Val
            20                  25                  30

Leu Gln Val Asn Leu Leu Ser Val Asn Tyr Gly Gly Pro Arg Leu Ala
        35                  40                  45

Ala Val Ala Asn Ala Gly Thr Ala Gly Leu Ile Ser Phe Glu Val Ser
    50                  55                  60

Pro Asp Ala Val Ala Glu Trp Gln Asn His Gln Ser Pro Glu Glu Ala
65                  70                  75                  80

Pro Ala Ala Val Ser Phe Arg Asn Leu Ala Tyr Gly Arg Thr Cys Val
                85                  90                  95

Leu Gly Lys Glu Leu Phe Gly Ser Ala Val Glu Gln Ala Ser Leu Gln
            100                 105                 110

Phe Tyr Lys Arg Pro Gln Gly Gly Ser Arg Pro Glu Phe Val Lys Leu
        115                 120                 125

Thr Met Glu Tyr Asp Asp Lys Val Ser Lys Ser His His Thr Cys Ala
130                 135                 140

Leu Met Pro Tyr Met Pro Ala Ser Asp Arg Leu Arg Asn Glu Gln
145                 150                 155                 160

Met Ile Gly Gln Val Leu Leu Met Pro Lys Thr Ala Ser Ser Leu Gln
                165                 170                 175

Lys Trp Ala Arg Gln Gln Gly Ser Gly Gly Val Lys Val Thr Leu Asn
            180                 185                 190

Pro Asp Leu Tyr Val Thr Thr Tyr Thr Ser Gly Glu Ala Cys Leu Thr
        195                 200                 205
```

```
Leu Asp Tyr Lys Pro Leu Ser Val Gly Pro Tyr Glu Ala Phe Thr Gly
        210                 215                 220

Pro Val Ala Lys Ala Gln Asp Val Gly Ala Val Glu Ala His Val Val
225                 230                 235                 240

Cys Ser Val Ala Ala Asp Ser Leu Ala Ala Leu Ser Leu Cys Arg
                245                 250                 255

Ile Pro Ala Val Ser Val Pro Ile Leu Arg Phe Tyr Arg Ser Gly Ile
                260                 265                 270

Ile Ala Val Val Ala Gly Leu Leu Thr Ser Ala Gly Asp Leu Pro Leu
        275                 280                 285

Asp Leu Ser Val Ile Leu Phe Asn His Ala Ser Glu Glu Ala Ala Ala
        290                 295                 300

Ser Thr Ala Ser Glu Pro Glu Asp Lys Ser Pro Arg Val Gln Pro Leu
305                 310                 315                 320

Gly Thr Gly Leu Gln Gln Arg Pro Arg His Thr Val Ser Pro Ser Pro
                325                 330                 335

Ser Pro Pro Pro Pro Arg Thr Pro Thr Trp Glu Ser Pro Ala Arg
                340                 345                 350

Pro Glu Thr Pro Ser Pro Ala Ile Pro Ser His Ser Ser Asn Thr Ala
            355                 360                 365

Leu Glu Arg Pro Leu Ala Val Gln Leu Ala Arg Lys Arg Thr Ser Ser
        370                 375                 380

Glu Ala Arg Gln Lys Gln Lys His Pro Lys Lys Val Lys Gln Ala Phe
385                 390                 395                 400

Asn Pro Leu Ile
```